(12) United States Patent
Earl et al.

(10) Patent No.: US 8,609,572 B2
(45) Date of Patent: Dec. 17, 2013

(54) BASIC IONIC LIQUIDS

(75) Inventors: Martyn J. Earl, Belfast (GB); Kenneth R. Seddon, Belfast (GB); Stewart Forsyth, Belfast (GB); Ute Frohlich, Belfast (GB); Nimal Gunaratne, Belfast (GB); Suhas Katdare, Belfast (GB)

(73) Assignee: The Queen's University of Belfast, Belfast (GB)

( * ) Notice: Subject to any disclaimer, the term of this patent is extended or adjusted under 35 U.S.C. 154(b) by 476 days.

(21) Appl. No.: 11/794,772

(22) PCT Filed: Jan. 4, 2006

(86) PCT No.: PCT/GB2006/000006
§ 371 (c)(1),
(2), (4) Date: Jun. 18, 2008

(87) PCT Pub. No.: WO2006/072775
PCT Pub. Date: Jul. 13, 2006

(65) Prior Publication Data
US 2009/0270248 A1 Oct. 29, 2009

(30) Foreign Application Priority Data
Jan. 4, 2005 (GB) .................... 0500029.4

(51) Int. Cl.
*B01J 31/00* (2006.01)
(52) U.S. Cl.
USPC .......................................... 502/150
(58) Field of Classification Search
None
See application file for complete search history.

(56) References Cited

U.S. PATENT DOCUMENTS

| 3,014,039 A | 12/1961 | Robinson et al. |
| 4,883,655 A | 11/1989 | Login et al. |
| 6,552,232 B2 | 4/2003 | Mehnert et al. |
| 6,774,240 B2 | 8/2004 | Seddon et al. |
| 7,208,605 B2 * | 4/2007 | Davis, Jr. ...................... 548/110 |
| 2002/0035297 A1 | 3/2002 | Favre et al. |
| 2004/0035293 A1 | 2/2004 | Davis, Jr. |
| 2004/0097755 A1 | 5/2004 | Abbott et al. |
| 2005/0245394 A1 * | 11/2005 | Dahar et al. ................. 502/439 |
| 2006/0079691 A1 | 4/2006 | Ignatyev et al. |
| 2011/0160460 A1 | 6/2011 | Michot et al. |

FOREIGN PATENT DOCUMENTS

| DE | 102 47 578 A1 | 4/2004 |
| EP | 0909770 | 4/1999 |
| JP | 6 321 897 | 11/1994 |

(Continued)

OTHER PUBLICATIONS

Cole et al, Novel bronsted acidic ionic liquids and their use as dual solvent-catalysts, 2002, j. am. chem. soc, 124, pp. 5962-5963.*

(Continued)

*Primary Examiner* — Melvin C Mayes
*Assistant Examiner* — Stefanie Cohen
(74) *Attorney, Agent, or Firm* — Marshall, Gerstein & Borun LLP

(57) ABSTRACT

Use of ionic liquids as solvents in base-catalysed chemical reactions wherein the ionic liquid is composed of at least one species of cation and at least one species of anion, characterized in that a cation of the ionic liquid comprises a positively charge moiety and a basic moiety, and further wherein such ionic liquids may be used as promoters or catalysts for the chemical reactions.

29 Claims, 2 Drawing Sheets

(56) References Cited

FOREIGN PATENT DOCUMENTS

Figure 1:
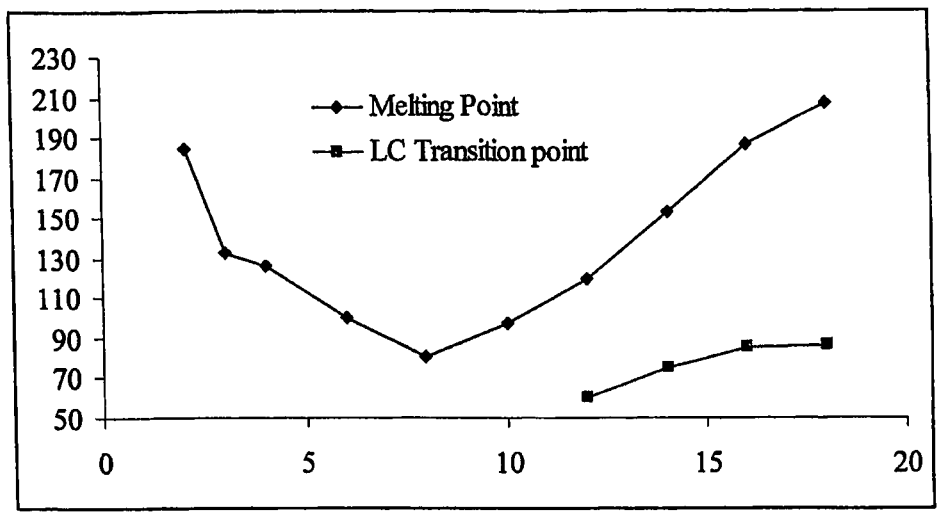

| | | |
|---|---|---|
| JP | 2001/527505 A | 12/2001 |
| JP | 2004 111184 | 4/2004 |
| WO | WO 00/56700 | 9/2000 |
| WO | WO 02/26381 | 4/2002 |
| WO | WO 02/26701 | 4/2002 |
| WO | WO 03/062171 | 7/2003 |
| WO | WO-03/086605 A2 | 10/2003 |
| WO | WO 2004/029004 | 4/2004 |
| WO | WO 2004/054991 | 7/2004 |
| WO | WO 2005/019185 | 3/2005 |
| WO | WO 2006/032716 | 3/2006 |
| WO | WO 2006/066790 | 6/2006 |

OTHER PUBLICATIONS

Buu-Hoi et al., "Further studies on the Knorr-Paal synthesis of 2,5-dialkylpyrroles", [Contribution from the Department of Organic Chemistry, Radium Institute, University of Paris], vol. 20, pp. 850-854 (1955).

Database CA Chemical Abstracts Service, Columbus, Ohio, US, Morris-Natschke, Susan L. et al., "Synthesis of phosphocholine and quaternary amine ether lipids and evaluation of in vitro antineoplastic activity" XP-2477667 & Journal of Medicinal Chemistry.

Database CA Chemical Abstracts Service, Columbus, Ohio, US. Abdullaev N. P. et al., "Synthesis of some bisquaternary salts of Ioline and Iolinine alkaloids"—XP2477668 & Khimiya Prirodnykh Soedinenii.

Database CA Chemical Abstracts Service, Columbus, Ohio, Deguchi, Yoshio, "Beta-Carboline derivatives. An attempt to synthesize benzindolequinolizines"—XP-2477669 & Igaku Shigen Kenkyusho Nempo.

European Examination Report dated Jun. 26, 2008 received in European Application No. 06 700 155.2-2104.

Abbott et al., "Quaternary ammonium zinc- or tin-containing ionic liquids: water insensitive, recyclable catalyst for Diels-Alder reactions", Green Chemistry, 4(1):24-26 (2002).

Abello et al., "Supported choline hydroxide (ionic liquid) as heterogeneous catalyst for aldol condensation reactions", Chem. Commun., 1096-1097 (2004).

Aggarwal et al., "Unexpected side reactions of imidazolium-based ionic liquids in the base-catalysed Baylis-Hillman reaction", Chem. Commun., 1612-1613 (2002).

Audic et al., "An ionic liquid-supported ruthenium carbene complex: a robust and recyclable catalyst for ring-closing olefin metathesis in ionic liquids", J. Am. Chem. Soc., 125(31):9248-9249 (2003).

Banks et al., "N-halogeno compounds, Part 17. Precursors of NF-TEDA reagents: quaternary salts of 1,4-diazabicyclooctane containing fluoro-anions, and their Lewis acid-Lewis base adducts with boron trifluoride, phosphorus pentafluoride and sulphur trioxide", Journal of Fluorine Chemistry, 78(1):43-50 (1996).

Bates et al., "$CO_2$ capture by a task-specific ionic liquid", J. Am. Chem. Soc., 124(6):926-927 (2002).

Branco et al., "Preparation and characterization of new room temperature ionic liquids", Chemistry—A European Journal, 8(16): 3671-3672 (2002).

Brauer et al., "Phosphines with 2-imidazolium and para-phenyl-2-imidazolium moieties-synthesis and application in two-phase catalysis", J. Organomet. Chem., 630(2):177-184 (2001).

Carmichael et al., "The Heck Reaction in Ionic Liquids: A multiphasic Catalyst System", Organic Letters, 1(7):997-1000 (1999).

Cooper et al., "Ionic liquids and eutectic mixtures as solvent and template in synthesis of zeolite analogues", Nature (London, United Kingdom, 430(7003):1012-1016 (2004).

Davis, "Task-Specific Ionic Liquids", Chemistry Letters, 33:1072-1077 (2004).

Earle et al., "The first high yield green route to a pharmaceutical in a room temperature ionic liquid", Green Chem., 2:261-262 (2000).

Earle et al., "Regioselective alkylation in ionic liquids", Chem. Comm., 2245-2246 (1998).

Earle, "Clean Synthesis in Ionic Liquids", Abstracts of Papers of the American Chemical Society, 221:161 (2001).

Forsyth et al., "Rapid, clean, and mild O-acetylation of alcohols and carbohydrates in an ionic liquid", Chem. Commun., 714-715 (2002).

Fraga-Dubreuil et al., "Grafted ionic liquid-phase-supported synthesis of small organic molecules", Tetrahedron Letters, 42(35):6097-6100 (2001).

Lall et al., "Polycations-12. The synthesis of liquid ionic phosphates (LIPs) from mono- and polycationic ammonium halides", Synthesis, 11:1530-1540 (2002).

Liu et al., [Bmim]NTf2, a low viscosity ionic liquid is a viable reaction medium for pd-catalyzed cross-coupling reactions, Synlett, 10:1814-1816 (2004).

Mateus et al., "Synthesis and properties of tetra-alkyl-dimethylguanidinium salts as a potential new generation of ionic liquids", Green Chem., 5:347-352 (2003).

McLachlan et al., "Palladium-Catalyzed Suzuki Cross-coupling reactions in ambient temperature ionic liquids: evidence for the importance of palladium imidazolylidene complexes", Organometallics, 22(25): 5350-5357 (2003).

Morales et al., "The regiospecific Fischer indole reaction in choline chloride-2ZnCl2 with product isolation by direct sublimation from the ionic liquid", Chemical Communications (Cambridge, United Kingdom), 2:158-159 (2004).

Rodriguez et al., "Catalytic composition for insertion of carbon dioxide into organic compounds", Chemical Abstracts Service, Database accession No. 2006:298814.

Sasaki et al., "A novel glycosidation of glycosyl fluoride using a designed ionic liquid and its effect on the stereoselectivity", Tetrahedron Letters, 45(38):7043-7047 (2004).

Sirieix et al., "Palladium Catalyzed Cross-Couplings of Organozincs in Ionic Liquids", Synlett, 11:1613-1615 (2000).

Welton et al., "Palladium catalyzed reactions in ionic liquids", Advances in Organometallic Chemistry, 51:251-284 (2004).

Xiao, "An ionic liquid-coordinated palladium complex: a highly efficient and recyclable catalyst for the Heck Reaction", Organic Letters, 3845-3847 (2004).

Xu et al., "Ionic Liquids: Ion Mobilities, Glass Temperatures, and Fragilities", Journal of Physical Chemistry B, 107(25):6170-6178 (2003).

Xu et al., "Ionic liquids of chelated orthoborates as model ionic glassformers", Journal of Physical Chemistry B, 107(42):11749-11756 (2003).

Zhao et al., "Synthesis and characterization of ionic liquids incorporating the nitrile functionality", Inorganic Chemistry, 43(6):2197-2205 (2004).

Zhou et al., "A new class of hydrophobic ionic liquids: trialkyl(2-methoxyethyl)ammonium perfluoroethyltrifluoroborate", Chemistry Letters, 33(7):886-887 (2004).

International Search Report for PCT/GB2006/000006 mailed Jan. 2, 2007.

Written Opinion for PCT/GB2006/000006 mailed Jan. 2, 2007.

Chinese Patent Application No. 200680005670.6—Examination Report issued Mar. 8, 2010 (Chinese language and English translation).

* cited by examiner

*Universal indicator TM in different bistriflimide ionic liquids*

*(a) BIL 1; (b) BIL 2; (c) BIL 2a; (d) BIL 4; concentration of UI is equal in all ILs.*

BASIC IONIC LIQUIDS

The present invention relates to ionic liquids and more specifically to novel basic ionic liquids and uses thereof as solvents in chemical reactions. The basic Ionic liquids, additionally, being capable of promoting, or catalysing, chemical reactions.

Aldol reactions which require base promotion or catalysis are described in U.S. Pat. No. 6,552,232, where 1,2,3-trialkylimidazolium salts or 1,3-dialkylimidazolium salts are used as solvents and/or catalysts for aldol reactions. U.S. Pat. No. 6,552,232 also describes the synthesis of imidazolium ionic liquids and uses thereof. However, the 1,2,3-trialkylimidazolium salts or 1,3-dialkylimidazolium salts are not stable under basic conditions and the $BF_4$ and $PF_6$ anions decompose to fluoride in the presence of acid or base. This decomposition of imidazolium ionic liquids under basic conditions is described in U.S. Pat. No. 6,774,240 and ACS Symposium Series 856, page 25 (where the instability of imidazolium hydroxides is exemplified). Further, the ionic salts of U.S. Pat. No. 6,552,232 are basic only due to the presence of hydroxyl groups as the anionic species.

M. J. Earle, K. R. Seddon, and P. B. McCormac, *Green Chem.*, 2000, 2, 261, and M. J. Earle, P. B. McCormac, and K. R. Seddon, *Chemical Communications*, 1998, 2245 describe the use of hydroxide base in ionic liquids to promote nucleophilic displacement reactions. However, as with U.S. Pat. No. 6,552,232, the basicity present is due to hydroxyl groups.

WO 03/062171 describes the use of the neutral molecule 1-methylimidazole for the removal of acids from a reaction mixture e.g. silylation of alcohols. The 1-methylimidazole/acid complex formed can be easily removed from the reaction mixture.

WO 04/029004 describes the synthesis of the basic ionic liquid N-(diethylaminobutyl)-trimethylammonoim bis triflamide for use in the Suzuki-coupling, where it is inferior in this reaction to simple bases such as potassium carbonate. The basic ionic liquid disclosed is not used as a solvent, but instead as a liquid support. The solvent, in contrast, is a regular, non-basic, ionic liquid.

Davis (Chemistry Letters, 2004, 33, 1072-1077) discloses that the basic ionic liquid 1-butyl-3-aminopropyl tetrafluoroborate reacts with carbon dioxide and that the amino group can chemically bond to reactants in a chemical process. The ionic liquid disclosed is not base stable as it comprises a base unstable imidazole ring in conjunction with a base unstable tetrafluoroborate anion.

Mateus, N. M. M. et. al. in Green Chem. 2003, 347 describes that some imidazolium ionic liquids can, be used in conjunction with a base, but Aggarwal, V. K. et. al. in Chem. Commun. 2002, 1612-1613 teaches us that imidazolium ionic liquids are unsuitable for base catalysed reactions (the Baylis-Hillman reaction in particular) because the imidazollum cation reacts with the reagents used under basic conditions. Earle, M. J. at the ACS symposium Washington D.C. 2001 (M. J. Earle, *Abstracts of Papers of the American Chemical Society,* 2001, 221, 161), also demonstrated that 2-alkylated imidazolium ionic liquids are unsuitable for base catalysed reactions because of side reaction resulting in the modification of the imidazolium cation.

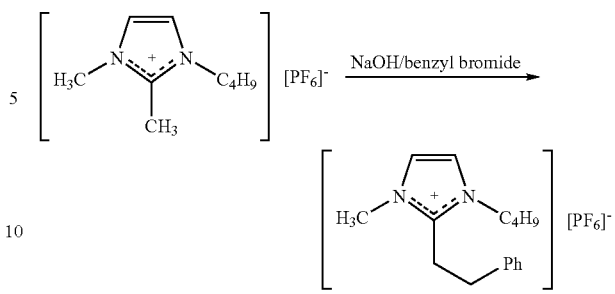

The reaction of 2-alkyl imidazolium ionic liquids in the presence of a base.

The term "ionic liquid" as used herein refers to a liquid that is capable of being produced by melting a solid, and when so produced, consists solely of ions. Ionic liquids may be derived from organic salts.

An ionic liquid may be formed from a homogeneous substance comprising one species of cation and one species of anion, or can be composed of more than one species of cation and/or anion. Thus, an ionic liquid may be composed of more than one species of cation and one species of anion. An ionic liquid may further be composed of one species of cation, and one or more species of anion. Thus the mixed salts of the invention can comprise mixed salts containing anions and cations.

Thus, in summary, the term "ionic liquid" as used herein may refer to a homogeneous composition consisting of a single salt (one cationic species and one anionic species) or it may refer to a heterogeneous composition containing more than one species of cation and/or more than one species of anion.

A class of ionic liquids which is of special interest is that of salt compositions with melting points below 100° C. Such compositions are mixtures of components which are often liquid at temperatures below the individual melting points of the components.

Ionic liquids where the anion gives rise to the ionic liquid's basicity have been disclosed by Forsyth, S. A. et. al in Chem. Commun. 2002, 714-715 for acetylation reactions, and by S. Abello et al. Chem. Commun. 2004. 1096-1097, for aldol reactions.

However ionic liquids where the cation gives rise to the basicity, together with application as solvents which, can also be used to promote, or catalyse reactions have not been disclosed.

The term "basic" refers to Bronsted bases having the ability to react with (neutralise) acids to form salts. The pH range of bases is from 7.0 to 14.0 when dissolved or suspended in water.

The present invention describes new uses of basic ionic liquids as solvents and in base catalysed or promoted chemical reactions, separations or processes. By utilizing ionic liquids as the reaction medium (i.e solvent) and/or catalyst it is possible to achieve higher selectivity, improved yields, simplified separation or purification of products, reduce or eliminate volatile solvents.

Unlike conventional solvent systems, these liquids exhibit low vapour pressure, tunable polarity and properties, and high thermal stability. Depending on the choice of ionic fragments, a reaction environment can be designed to accommodate the catalysis and the separation of a chemical process in the most efficient way. By combining base catalysis with the advantages of ionic liquids, it is possible to prepare catalyst media which, exhibit significant advantages of selectivity and recyclability over existing catalyst systems.

According to one aspect of the present invention, there is provided the use of an ionic liquid as a solvent in a base-catalysed chemical reaction, the ionic liquid being composed of at least one species of cation and at least one species of anion, characterized in that a cation of the ionic liquid comprises (i) a positively charged moiety and (ii) a basic moiety.

The basic ionic liquids for use in the present invention may be represented by the formula:

[Cat$^+$-Z-Bas][X$^-$]

wherein:
Cat$^+$=positively charged moiety:
Bas=basic moiety; and
Z=a covalent bond joining Cat$^+$ and Bas, or 1, 2 or 3 aliphatic divalent linking groups each containing 1 to 10 carbon atoms and each optionally one, two or three oxygen atoms.
X$^-$=anion Preferably, Bas comprises at least one nitrogen, phosphorus, sulphur, oxygen or boron atom, for example, Bas may comprise at least one primary, secondary or tertiary amino group.

Bas as defined herein does not include —OH, as it is not considered basic in the context of the present invention, due to difficulties with protonation. More preferably, Bas does not include —OH and —OR$_1$.

Preferably, Bas is selected from —N(R$_1$)(R$_2$), and —P(R$_1$)(R$_2$)(R$_3$); and wherein R$_1$, R$_2$ and R$_3$ can be the same or different and are each independently selected from hydrogen, linear or branched alkyl, cycloalkyl, aryl and substituted aryl.

Preferably, R$_1$, R$_2$ and R$_3$ are each selected from hydrogen, methyl, ethyl, isopropyl, propyl, butyl, sec-butyl, isobutyl, pentyl, hexyl, cyclohexyl, benzyl and phenyl.

Still more preferably, Bas is —N(CH$_3$)$_2$ or —N(CH(CH$_3$)$_2$)$_2$.

Another aspect of the present invention is directed to use of compounds which are basic ionic liquids and wherein Bas is a hindered basic moiety.

The term "hindered basic moiety" refers to a functional group that acts as a base, but because of steric hinderance, does not chemically bond to the reagents or products.

For hindered basic ionic liquids the group R should have low nucleophilicity such as that described for Hunig's base (bis-(diisopropyl)ethylamine) (see Tetrahedron Letters 1981, 31, 1483). Also in this respect, reference is made to paper, "Hindered non-nuclepohilic base with high protein affinity", Chem. Ber. 1958, 91, p 380 ad Chem. Ber., 1993, 29, p 1042. This means that the basic group R is capable of forming a chemical bond with free hydrogen ions, but does not form chemical bonds with the reagents or products in a chemical process.

The Bas moiety should have lower nucleophilicity or greater steric hinderance than that given be three ethyl groups attached to the nitrogen as disclosed in WO 04/029004.

In accordance with the present invention Z may be selected from linear or branched C$_1$ to C$_{18}$ alkanediyl, substituted alkanediyl, dialkanylether or dialkanylketone, preferably C$_1$ to C$_8$ and more preferably C$_2$ to C$_6$.

Preferably, Z is selected from —(CH$_2$—CH$_2$)—, (CH$_2$—CH$_2$—CH$_2$)—, —(CH$_2$—CH$_2$—CH$_2$—CH$_2$)—, —(CH$_2$—CH$_2$—CH$_2$—CH$_2$—CH$_2$)—, —(CH$_2$—CH$_2$—CH$_2$—CH$_2$—CH$_2$—CH$_2$)—, —(CH$_2$—CH$_2$—O—CH$_2$—CH$_2$)— and —(CH$_2$—CH$_2$—O—CH$_2$—CH$_2$—CH$_2$)—.

The Cat$^+$ moiety may comprise or consist of a heterocyclic ring structure selected from imidazolium, pyridinium, pyrazolium, thiazolium, isothiazolinium, azathiozolium, oxothiazolium, oxazinium, oxazolium, oxaborolium, dithiazolium, triazolium, selenozolium, oxaphospholium, pyrollium, borolium, furanium, thiophenium, phospholium, pentazolium, indolium, indolinium, oxazolium, isooxazolium, isotriazolium, tetrazolium, benzofuranium, dibenzofuranium, benzothiophenium, dibenzothiophenium, thiadiazolium, pyrimidinium, pyrazinium, pyridazinium, piperazinium, piperidinium, morpholinium, pyranium, annolinium, phthalazinium, quinazolinium, quinazalinium, quinolinium, isoquinolinium, thazinium, oxazinium and azaannulenium.

Preferred Cat$^+$-Z-Bas in accordance with the present invention may be selected from:

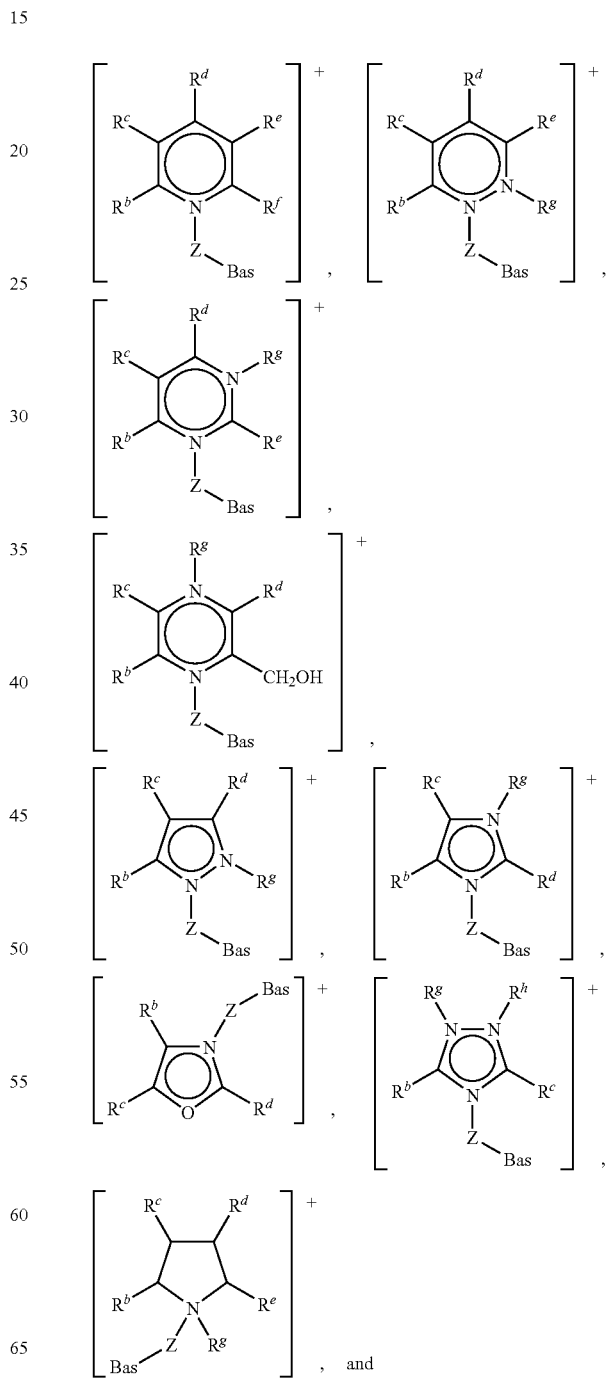

, and

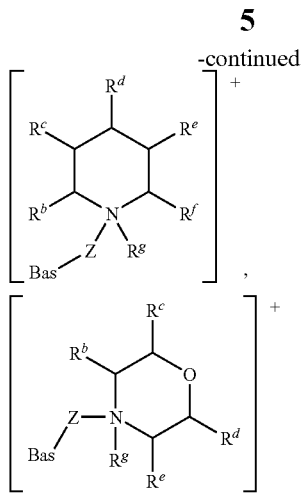

wherein: Bas and Z are as defined above; and
$R^b$, $R^c$, $R^d$, $R^e$, $R^f$, $R^g$ and $R^h$ can be the same or different, and are each independently selected from hydrogen, a $C_1$ to $C_{40}$, straight chain or branched alkyl group, a $C_3$ to $C_8$ cycloalkyl group, or a $C_6$ to $C_{10}$ aryl group, wherein said alkyl, cycloalkyl or aryl groups are unsubstituted or may be substituted by one to three groups selected from: $C_1$ to $C_6$ alkoxy, $C_6$ to $C_{10}$ aryl, CN, OH, $NO_2$, $C_7$ to $C_{30}$ aralkyl and $C_7$ to $C_{30}$ alkaryl, or any two of $R^b$, $R^c$, $R^d$, $R^e$ and $R^f$ attached to adjacent carbon atoms form a methylene chain —$(CH_2)_q$— wherein q is from 8 to 20.

More preferably Cat⁺-Z-Bas is selected from:—

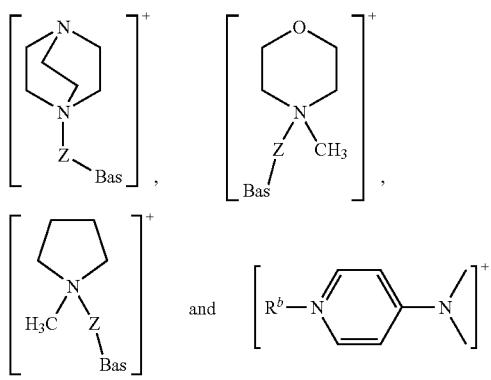

wherein: Bas, Z and $R^b$ are as define above.

Still more preferably, Cat⁺-Z-Bas may be selected from the group consisting of:—

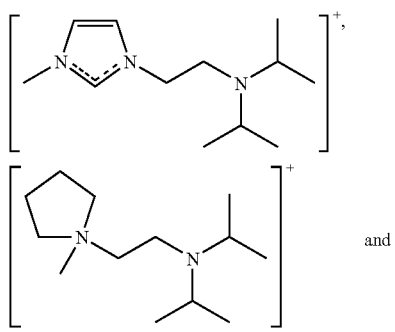

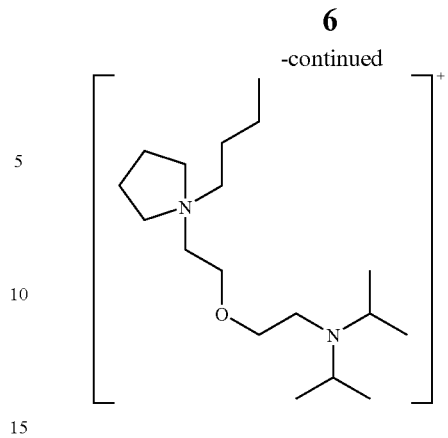

(all of the compounds above being considered "hindered")

The Cat⁺ moiety for use in the present invention may be obtained by alkylation, protonation and/or acylation of a precursor selected from imidazoles, pyridines, pyrazoles, thiazoles, isothiazoles, azathiozoles, oxothiazoles, oxazines, oxazolines, oxazoboroles, dithiozoles, triazoles, selenozoles, oxaphospholes, pyrroles, boroles, furans, thiophenes, phospholes, pentazoles, indoles, indolines, oxazoles, isooxazoles, isotriazoles, tetrazoles, benzofurans, dibenzofurans, benzothiophenes, dibenzothiophenes, thiadiazoles, pyrimidines, pyrazines, pyridazines, piperazines, piperidines, morpholines, pyrans, annolines, phthalazines, quinazolines, quinazalines, quinolines, isoquinolines, thazines, oxazines, and azaannulenes.

In accordance with the present invention, the Cat⁺ moiety may also be an acyclic organic ion.

Where the Cat⁺ moiety is acyclic, it preferably comprises or consists of a group selected from amino amidino, imino, guanidino, phosphino, arsino, stibino, alkoxyalkyl, alkylthio, alkylseleno and phosphinimino.

Where the Cat⁺ moiety is acyclic, Cat⁺-Z-Bas is preferably selected from:

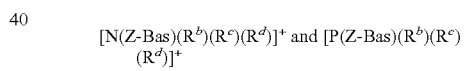

wherein: Bas, Z, $R^b$, $R^c$, and $R^d$ are as defined above

Where Cat⁺ is an acyclic moiety, Bas is preferably not —OH, as the group, in the context of the present ionic liquids, is not considered basic.

More preferably, Cat⁺-Z-Bas is selected from:

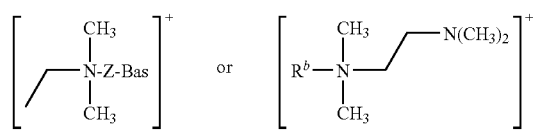

wherein: Bas, Z and Rb are as defined above.

Still more preferably, Cat⁺-Z-Bas is selected from:

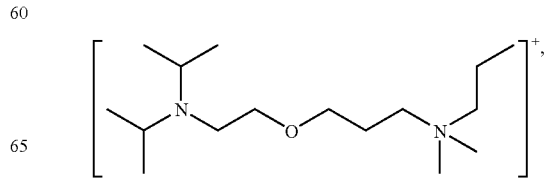

-continued

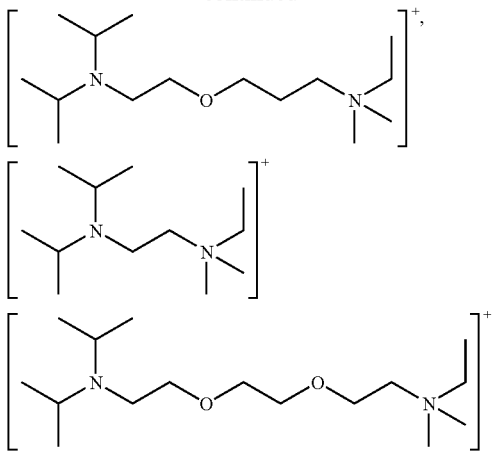

(all of the above compounds being considered "hindered" basic ionic liquids)

and 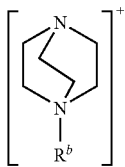

In accordance with the present invention, Cat⁺-Z-Bas may also be:

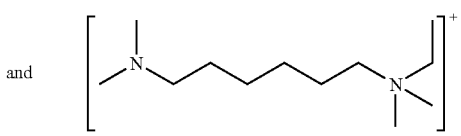

wherein: Rb is as defined above

In accordance with any aspect of the present invention, the anion $X^-$ may be an alkylated or halogenated salt of a Group IB, IIIA, IVA, VA, VIA or VIIA element.

$X^-$ is preferably selected from hydroxide, alkoxide, phenoxide, dicyanamide, borate, phosphate, nitrate, sulfate, triflate, halogenated copperate, antimonate, phosphite, substituted and unsubstituted metalloborane, substituted and unsubstituted carboxylate and triflate; or mixtures thereof.

More preferably, $X^-$ is selected from $BF_4$, $PF_6$, $CF_3SO_3$, $CF_3COO$, $SbF_6$, $CuCl_2$, $A_5F_6$, $SO_4$, $CF_3CH_2CH_2COO$, $(CF_3SO_2)_3C$, $CF_3(CF_2)_3SO_3$, $[CF_3SO_2]_2N$ and a metal inorganic anion.

Still more preferably, $X^-$ is selected from halide, trilate, bistrdluoromethanesulfonylamide $[(CF_3SO_2)_2N]$ and alkylsulfonate $[RSO_3]$.

As noted above, the ionic liquid may comprise a mixture of one or more cations having a basic moiety and a positively charged moiety.

The ionic liquid may further comprise a mixture of one or more anions.

The ionic liquid may further comprise a mixture of one or more ionic liquids composed of a cation and an anion.

In a further aspect of the present invention, the ionic liquid may further comprise one or more basic anions.

The basic anion may be represented by the formula:

[X—R-Bas]⁻

Wherein:
X and Bas are as defined above; and
R is a covalent bond joining X and Bas, or a linking group comprising 1 to 10 carbon atoms and optionally one, two or three oxygen atoms.

Preferably, R is selected from —(CH₂—CH₂)—, (CH₂—CH₂—CH₂)—, —(CH₂—CH₂—CH₂—CH₂)—, —(CH₂—CH₂—CH₂—CH₂—CH₂)—, —(CH₂—CH₂—CH₂—CH₂—CH₂—CH₂)—, —(CH₂—CH₂—O—CH₂—CH₂)— and —(CH₂—CH₂—O—CH₂—CH₂—CH₂)—.

In accordance with yet another aspect of the present invention, the Cat⁺ moiety may be selected from those disclosed above and the anionic species $X^-$ may also a basic ion.

Such basic ionic liquid is typically formed by reacting an ionic liquid precursor with either an alkali metal hydroxide or alkali earth metal hydroxide in a solvent medium with the loss of a salt, as is known by one skilled in the art. The most preferred anionic species are those prepared from potassium hydroxide or sodium hydroxide.

The basic ionic liquids of the present invention may be used in a range of chemical reactions. The chemical reactions include the Heck Reaction, Suzuki Coupling, nucleophilic displacement reactions, hydrolysis, esterification, transesterification aldol reactions, epoxidation, hydrogenation, condensation, oxidation reduction, hydration, dehydration, substitution, aromatic substitution, addition (including to carbonyl groups), elimination, polymerisation, depolymerisation, oligomerisation, dimersiation, coupling, electrocyclic, isomerisation, carbene formation, epimerisation, inversion, rearrangement, photochemical, microwave assisted, thermal, sonochemical and disproportionation reactions.

The basic ionic liquids of the present invention may also be used to catalyse and/or promote reactions, such as those listed above.

The term "catalyst" is used herein to include all forms of catalysis, including classic initiators, co-initiators, co-catalysts, activating techniques, etc.

The above-referenced processes may be generally carried out at a pressure of from about 1 atm (atmospheric pressure) to about 1000 atm (elevated pressure). The reaction can be carried out over a wide range of temperatures and is not particularly limited. Usually the reaction temperature is within the range of from about −50° C. to 400° C., more typically within the range of from 0° C. to 250° C., such as from 20° C. to 150° C.

The aldol condensation reactions of the instant case may run for approximately from about 0.01 to 1000 hours, preferably from about 0.1 to 100 hours, and most preferably for about 1 to 10 hours.

Another aspect of the present invention is directed to basic ionic liquids of formula:

[Cat⁺-Z-Bas][X⁻]

wherein:
Cat⁺=a positively charged moiety comprising or consisting of a heterocyclic ring structure selected from pyridinium, pyrazolium, thiazolium, isothiazolinium, azathiozolium, oxothiazolium, oxazinium, oxazolium, oxaborolium, dithiazolium, triazolium, selenozolium, oxaphospholium, pyrollium, borolium, furanium, thiophenium, phospholium, pentazolium, indolium, indolinium, oxazolium, isooxazolium, isotriazolium, tetrazolium, benzofuranium, dibenzofuranium, benzothiophenium, dibenzothiophenium, thiadiazolium, pyrimidinium, pyrazinium, pyridazinium, piperazinium, piperidinium, morpholinium, pyranium, annolinium, phthalazinium, quinazolinium, quinazalinium, quinolinium, isoquinolinium, thazinium, oxazinium and azaannulenium;

Z=a covalent bond joining Cat⁺ and Bas, or 1, 2 or 3 aliphatic divalent linking groups each containing 1 to 10 carbon atoms and each optionally one, two or three oxygen atoms;

X⁻=is selected from alkoxide, phenoxide, dicyanamide, borate, nitrate, sulfate, triflate, halogenated copperate, antimonate, phosphite, substituted and unsubstituted metalloborane, substituted and unsubstituted carboxylate and triflate, or mixtures thereof; and Bas=basic moiety as defined above.

Z may be selected from linear or branched $C_1$ to $C_6$ alkanediyl, substituted alkanediyl, dialkanylether or dialkanylketone. Preferably, Z is selected from —(CH₂—CH₂)—, (CH₂—CH₂—CH₂)—, —(CH₂—CH₂—CH₂—CH₂)—, —(CH₂—CH₂—CH₂—CH₂—CH₂)—, —(CH₂—CH₂—CH₂—CH₂—CH₂—CH₂)—, —(CH₂—CH₂—O—CH₂—CH₂)— and —(CH₂—CH₂—O—CH₂—CH₂—CH₂)—.

The basic ionic liquid is preferably selected from a compound of formula:

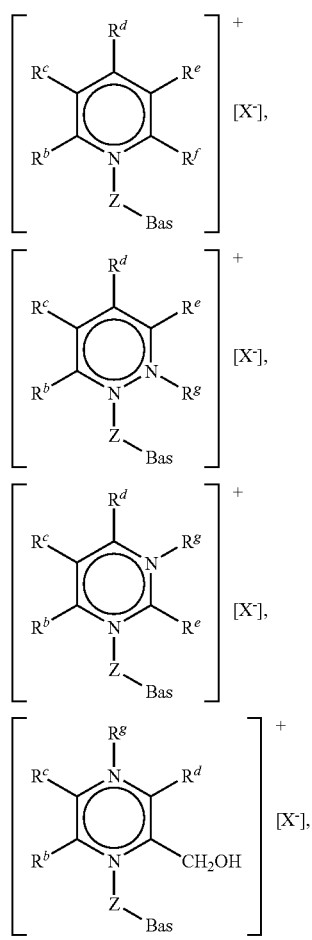

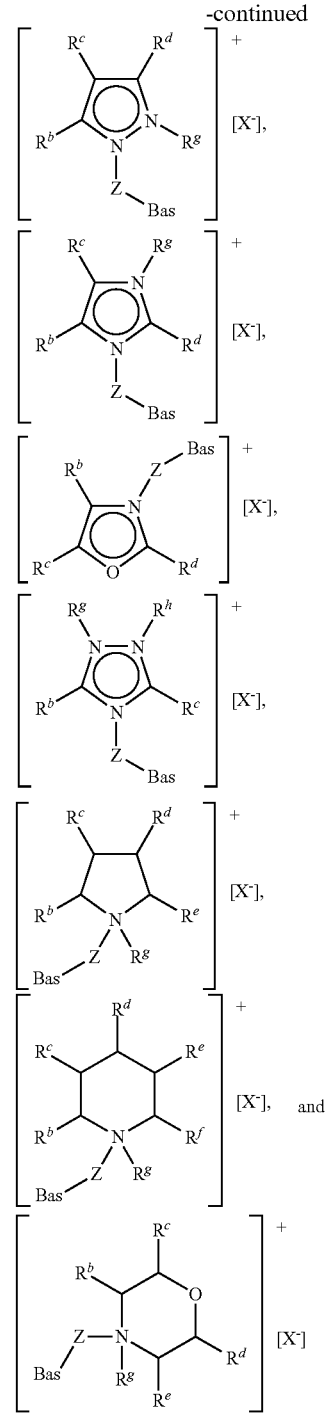

wherein: Bas, Z and X⁻ are as defined above; and $R^b$, $R^c$, $R^d$, $R^e$, $R^f$, $R^g$ and $R^h$ can be the same or different, and are each independently selected from hydrogen, a $C_1$ to $C_{40}$, straight chain or branched alkyl group, a $C_3$ to $C_8$ cycloalkyl group, or a $C_6$ to $C_{10}$ aryl group, wherein said alkyl, cycloalkyl or aryl groups are unsubstituted or may be substituted by one to three groups selected from: $C_1$ to $C_6$ alkoxy, $C_6$ to $C_{10}$ aryl, CN, OH, NO₂, $C_7$ to $C_{30}$ aralkyl and $C_7$ to $C_{30}$ alkaryl, or any two of $R^b$, $R^c$, $R^d$, $R^e$ and $R^f$ attached to adjacent carbon atoms form a methylene chain —(CH₂)$_q$— wherein q is from 8 to 20.

Preferably, the basic ionic liquid is selected from:

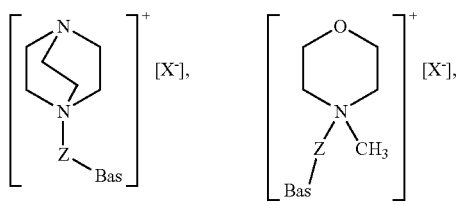

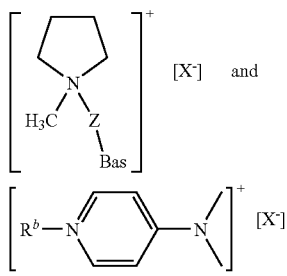

wherein: Bas, $X^-$ and $R^b$ are as defined above.

More preferably, the basic ionic liquid is selected from a compound of formula:

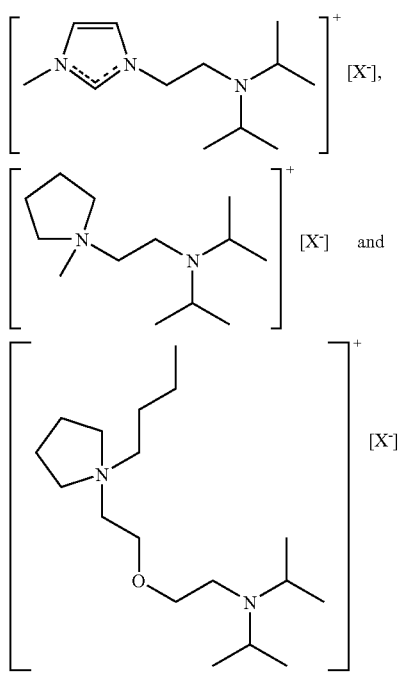

In yet another aspect of the present invention, the basic ionic liquid is selected from compounds of formula:
[Cat$^+$-Z-Bas][X$^-$]
wherein:
  Cat$^+$=acyclic positively charged moiety;
  Z=a covalent bond joining Cat$^+$ and Bas, or 1, 2 or 3 aliphatic divalent linking groups each containing 1 to 10 carbon atoms and each optionally one, two or three oxygen atoms;
  X$^-$=anion;
  Bas=—N(R$_1$)(R$_2$), —P(R$_1$)(R$_2$)(R$_3$), —PO(OR$_1$), PO(OR$_1$)(OR$_2$), —S(R$_1$), —SO$_2$(OR$_1$), and boron containing groups, wherein R$_1$, R$_2$ and R$_3$ can be the same or different and are each independently selected from hydrogen, linear or branched alkyl, cycloalkyl, aryl and substituted aryl; with the proviso that Bas is not —NH$_2$, —NHMe, N(Et)$_2$, or boratrane; and with the proviso that where Cat$^+$ comprises an amino group, the anion X$^-$ is selected from dicyanamide, borate, phosphate, nitrate, sulfate, triflate, halogenated copperate, antimonate, phosphite, substituted and unsubstituted metalloborane and mixtures thereof.

Preferably the acyclic ionic liquid is selected from a compound of formula:

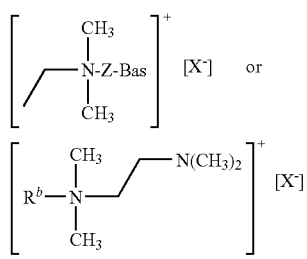

wherein: Bas, Z, $X^-$ and $R^b$ are as defined above.
More preferably, the ionic liquid is selected from:

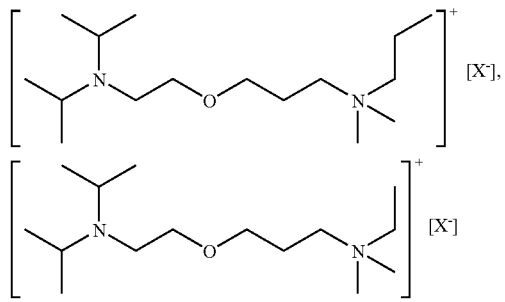

(both of the above compounds being considered "hindered" basic ionic liquids)

and 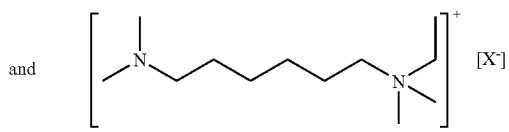

Still yet another aspect of the present invention is directed to a basic ionic liquid of formula:

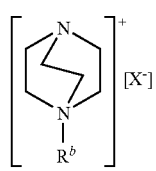

wherein: $X^-$ and $R^b$ are as defined above
In accordance with any aspect of the present invention, the basicity (or base strength) of a basic ionic liquid can be altered, by adjusting the distance between the cationic centre and the basic group. A separation of distances corresponding to (approximately) 2 methylene groups gives a mild basic ionic liquid. A separation of 6 methylene groups (or similar distance to that or 6 methylene groups) gives a stronger basic ionic liquid. Hence in this invention, the base strength of the ionic liquid can be adjusted.

In the present invention, the ionic liquid phase can be recycled by way of methods known in the art and applied as reaction medium to form products. The ionic liquid medium may also be recycled for use in other reactions.

The present invention will now be described and discussed by way of the following examples:

EXAMPLE 1

Dabco Ionic Liquids

The reaction of an alkyl halide with excess diazabicyclo[2,2,2]octane gives a basic series of ionic liquids.

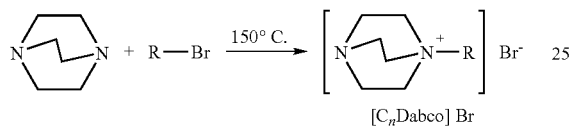

The mono alkyl DABCO bromides have fairly high melting points, but the hexyl, octyl and decyl DABCO bromides are ionic liquids (m.p. <100° C.). The decomposition temperatures are all in the 220-250° C. range by DSC. The melting point of the $C_6$DABCO bromide ionic liquid (95° C.) fell to 25° C. for the [C6DABCO][N(SO$_2$CF$_3$)$_2$] which formed a gel at this temperature (see FIG. 1).

Ethyl DABCO methanesulfonate [C$_2$DABCO][OSO$_2$CH$_3$] (mp 81° C.) and hexyl DABCO methanesulfonate have also been synthesised from the reaction of DABCO and ethylmethanesulfonate or hexylmethanesulfonate.

Typical Experimental Procedure

[C$_n$DABCO]Br

Diazobicyclo-[2,2,0]-octene (1.13 g, 12.5 mmol) and alkyl bromide (10 mmol) were heated under reflux (or at 150° C. which ever is the lower) for 1 to 24 hours. On cooling a precititate formed. This was dissolved in a minimum quantity boiling ethyl acetate/isopropanol for C2 to C10 DABCD bromides and boiling toluene/ethyl acetate for C12 to C18 DABCO bromides. The crystals that formed on cooling were filtered off and dried by heating at 80° C. for 4 hours under vacuum (1 mmHg). The compounds were analysed by NMR and DSC. Yields typically 60-80%

[C$_n$DABCO][OSO$_2$CH$_3$]

Diazobicyclo-[2,2,0]-octene (1.13 g, 12.5 mmol) and alkyl methanesulfonate (10 mmol) were heated at 100° C. for 1 hour. On cooling a precititate formed. This was dissolved in a minimum quantity boiling ethyl acetate/isopropanol. The crystals that formed on cooling were filtered off and dried by heating at 80° C. for 4 hours under vacuum (1 mmHg). The compounds were analysed by NMR and DSC. Yields typically 70-80%.

[C$_n$DABCO][N(SO$_2$CF$_3$)$_2$]

[C$_6$DABCO]Br (2.75 g, 10.0 mmol) and lithium bisftrifluoromethanesulfinimide (3.15 g, 11 mmol) were each dissolved in water (10 cm$^3$). The two solutions were mixed and a dense ionic liquid phase formed. This was extracted with dichloromethane (3×10 cm$^3$), dried over Na$_2$SO$_4$, filtered and the solvent evaporated to give a colourless paste, which became liquid at 25° C. This paste was dried by heating at 80° C. for 4 hours under vacuum (1 mmHg). The compounds were analysed by NMR and DSC.

EXAMPLE 2

TMEDA Salts

Tetramethylethylenediamine (TMEDA) ionic liquids are synthesised from TMEDA and an alkyl bromide as below. The C$_2$, C$_5$, C$_6$, C$_8$, C$_{12}$ and C$_{18}$ alkyl bromides have been made and [C$_n$TMEDA]Br where n=5, 6, 8, 10 are room temperature ionic liquids.

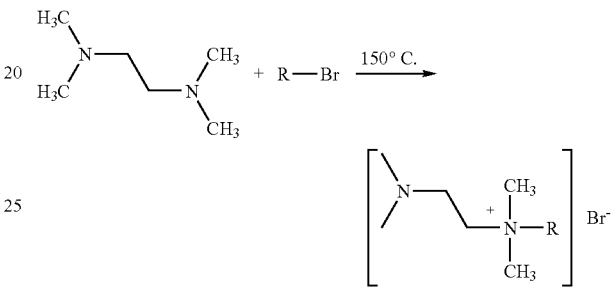

Synthesis of TMEDA Ionic Liquids.

[C$_n$TMEDA]Br

Tetramethylethylenediamine (TMEDA) (2.32 g, 20 mmol) and alkyl bromide (25 mmol) were heated under reflux (or at 130° C. which ever is the lower) for 1 hour resulting in a dense phase forming. This was cooled to room temperature. For [C$_2$TMEDA]Br and [C$_4$TMEDA]Br a crystalline solid formed and for [C$_{18}$TMEDA]Br, a liquid crystalline material formed. These products were washed with cyclohexane and dried under vacuum (24 h at 80° C., 1 mmHg). Yields typically 60-80%

EXAMPLE 3

DMAP Salts

N,N-dimethylaminopyidine (DMAP) ionic liquids are synthesised from DMAP and an alkyl methanesulfonate as below.

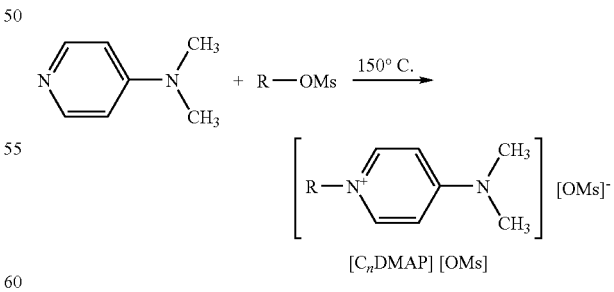

Synthesis of New DMAP Ionic Liquids.

Dimethylaminopyridine (DMAP) (2.443 g, 20 mmol) and either ethyl or hexyl bromide (25 mmol) were heated under reflux (or at 130° C. which ever is the lower) for 1 hour. On cooling a precititate formed. This was dissolved in a minimum quantity boiling ethyl acetate/isopropanol for C$_2$ to C$_6$ DMAP bromides. The crystals that formed on cooling were filtered off and dried by heat at 80° C. for 4 hours under vacuum (1 mmHg). The compounds were analysed by NMR and DSC. Yields typically 60-80%.

Dimethylaminopyridine (DMAP) (2.443 g, 20 mmol) and either ethyl or hexyl methanesulfonate (25 mmol) were heated at 100° C. for 1 hour. On cooling a precititate formed. This was dissolved in a minimum quantity boiling ethyl acetate/isopropanol for $C_2$ to $C_6$ DMAP methanesulfonates. The crystals that formed on cooling were filtered off and dried by heat at 80° C. for 4 hours under vacuum (1 mmHg). The compounds were analysed by NMR and DSC. Yields typically 80-85%.

EXAMPLE 4

Sodium hydride (60% dispersion in oil) (45 mmol, 1.80 g) was added portionwise to a solution of N,N-dimethylethanolamine (20 mmol, 1.78 g) in THF (100 cm³). The resultant slurry was heated at 60° C. for 1 hour then cooled. 1-(N-morpholino)-2-chloroethane hydrochloride (20 mmol, 3.72 g) was added portionwise and the slurry stirrer at 25° for 18 hours. Ethanol (10 cm³) followed by water (100 cm³) was added and the product was extracted with dichloromethane (3×50 cm³). The dichloromethane extracts were dried over Na2SO4, filtered and concentrated on a rotary evapourator. The product was Kugelrorh distilled at 110-120° C., 1 mmHg to give 2.3 g of a colourless oil (N-morpholinoethyl dimethylaminoethyl ether).

Diisopropylethylamine (Hünig's base) is known to be a non-nucleophilic base, this functional group was incorporated into an ionic liquid. 1-Chloro-2-(diisopropylamino)ethane hydrochloride is commercially available and was use to quaternise methylimidazole, yielding the imidazolium cation with a diisopropylamino group in the side chain (below).

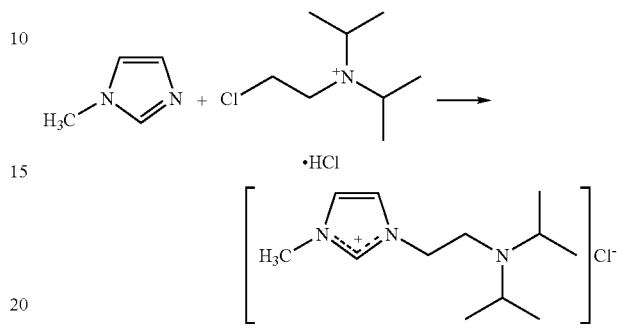

Synthesis and Structure of methyl-(2-diisopropylamino)-imiazolium chloride

The metathesis reaction with lithium bistriflimide yielded a room temperature ionic liquid that was insoluble in water. This ionic liquid acted as a mild base.

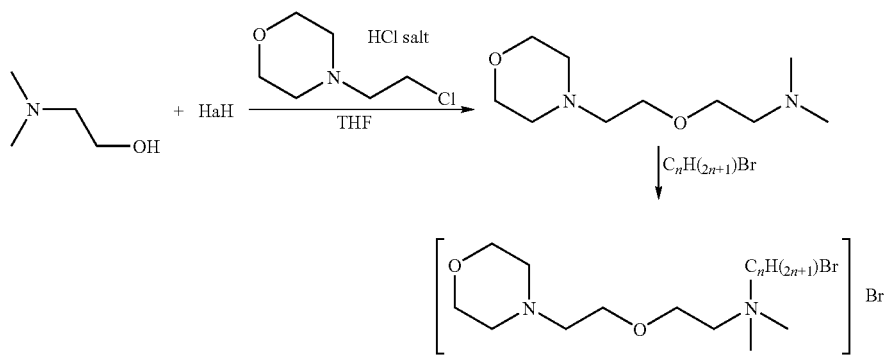

EXAMPLE 5

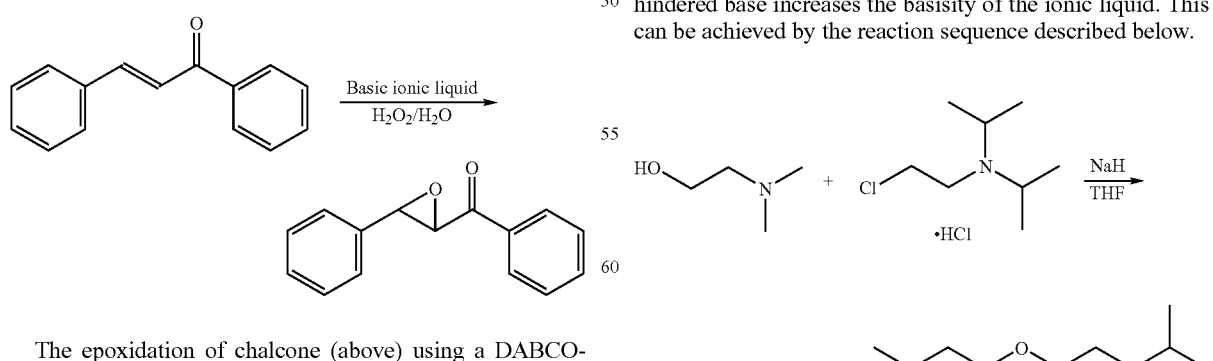

The epoxidation of chalcone (above) using a DABCO-based basic ionic liquid as a base showed a very slow reaction. It was assumed that the trialkylamine group of the ionic liquid was to nucleophilic and formed an N-oxide in presence of hydrogen peroxide rather that acting as a Brønsted base.

EXAMPLE 6

Increasing the distance between the cationic centre and the hindered base increases the basisity of the ionic liquid. This can be achieved by the reaction sequence described below.

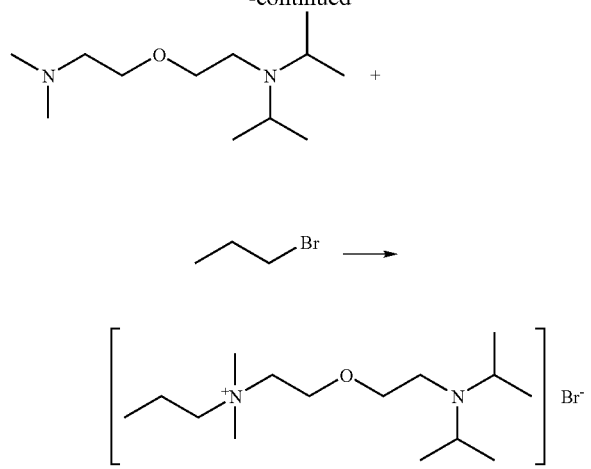

Synthesis of an Ionic Liquid with a Longer Distance Between Cation and the Basic Group The 1-chloro-2-(diisopropylamino)ethane hydrochloride was used to alkylate dimethylaminoethanol, the resulting diamine was alkylated with propyl bromide. The quaternisation reaction itself is regiospecific, the diisopropylamino group is non-nucleophilic and cannot be quaternised under the applied conditions. The obtained salt shows a five atom chain between the cation and the basic diisopropylamino group. The metathesis reaction with lithium bistriflimide gave a room temperature ionic liquid. Its structure is shown in below.

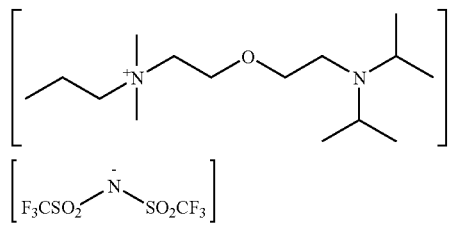

The epoxidation reaction of chalcone was carried out in this ionic liquid and gave 100% conversion. The substrate was dissolved in the ionic liquid phase and an aqueous phase containing hydrogen peroxide was added.

EXAMPLE 7

Figure 2:
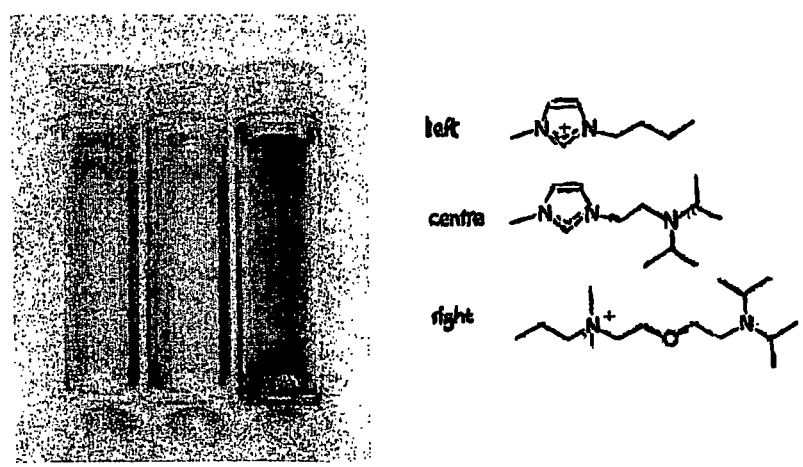

The determination of the absolute basicity of an ionic liquid is not trivial because the Brønsted basicity scale is based on water as a medium. A dry ionic liquid does not contain any water, yet it can act as an acid or base. In order to assess the relative basicity to compare ionic liquids, a colour indicator was used. Universal indicator TM, used for PH paper, is also available as a solution. It contains a range of indicator molecules which change colour according to whether they are protonated or not, covering the whole pH range in water with specific colours. When dissolved in an ionic liquid in the absence of water, these indicators also change colour, although their colours do not correspond to the conventional pH-values. But an ionic liquid showing a blue colour would still indicate more basic properties than an Ionic liquid showing a yellow or orange colour. FIG. 2 shows a picture of three different bistriflimide ionic liquids after addition of a defined amount of indicator followed by evaporation of the solvent. The sample on the left shows [bmim][NTf$_2$], in the centre is methyl-(2-diisopropylamino)-imiazolium [NTf$_2$], both containing the same concentration of indicator. According to their colour they seem to possess a similar basicity.

FIG. 2 shows the indicator in an ionic liquid with a five atom chain between the base and the cation, its colour is shifted towards blue, indicating stronger basic properties. This ionic liquid did act as a good base catalyst (and solvent) in the chalcone epoxidation reaction.

EXAMPLE 8

The synthesis of a basic ionic liquid based on methylpyrrolidine is shown below.

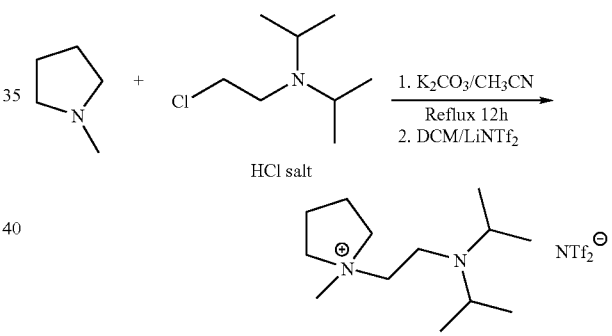

The Synthesis of a Hindered Basic Ionic Liquid N-methyl-N-(bisdiisopropyl)aminoethyl pyrrolidinium bistriflamide The above scheme shows the synthesis of an ionic liquid bearing a two carbon spacer between the quaternary nitrogen and the basic nitrogen. The DSC of the basic ionic liquid indicates that the melting point of the ionic liquid is −27° C.

EXAMPLE 9

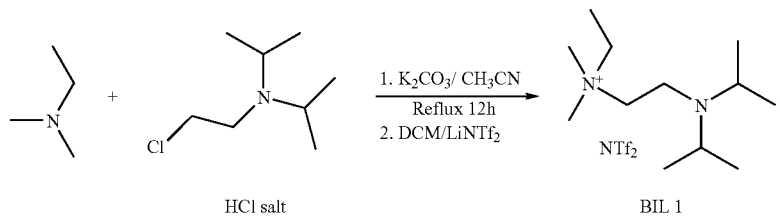

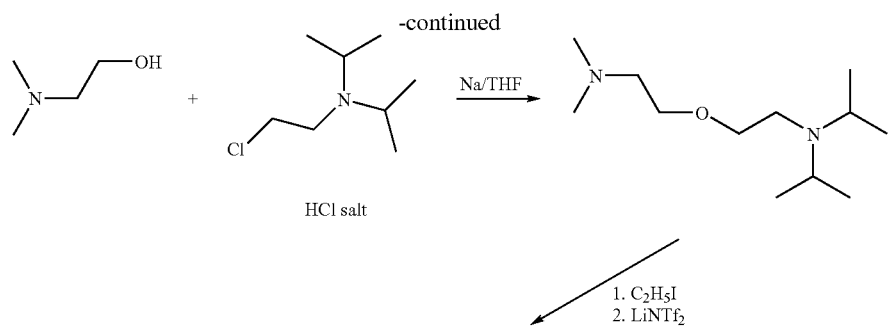

HCl salt

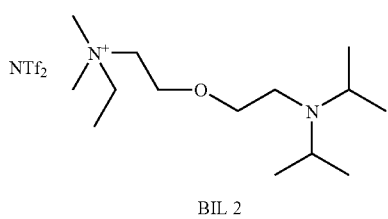

BIL 2

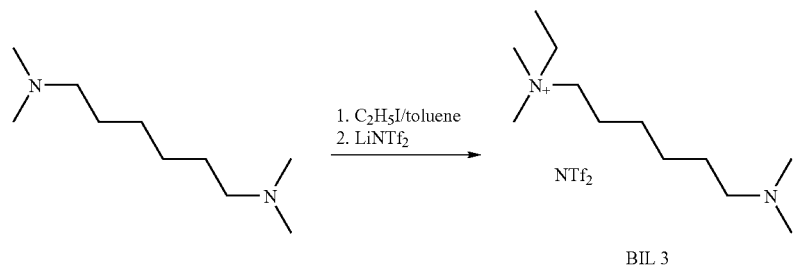

BIL 3

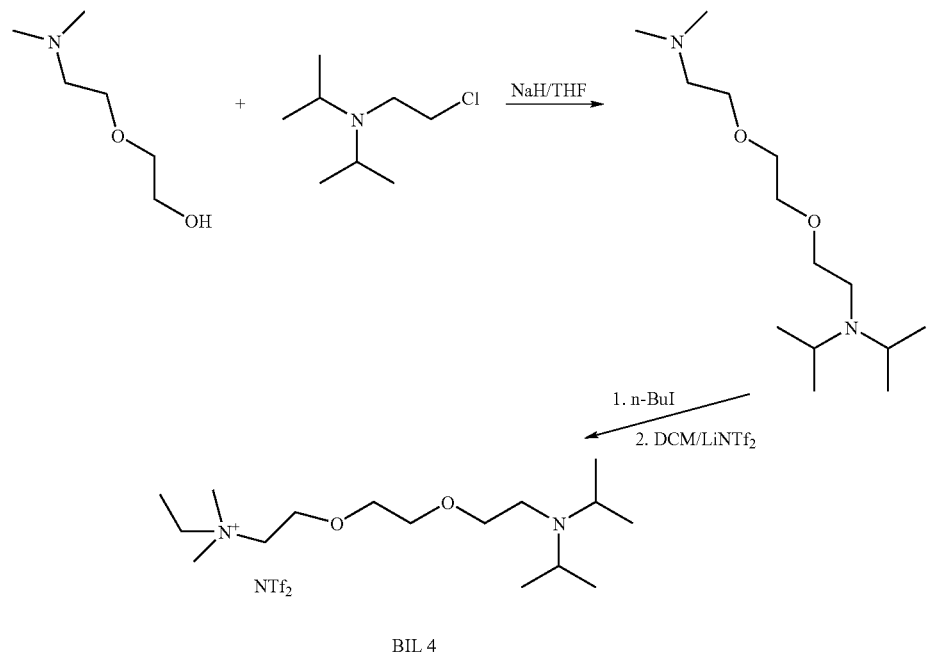

BIL 4

The above scheme shows a synthesis of a range of basic ionic liquids, for example, bearing a 5-atom spacer between the quaternary nitrogen and the basic nitrogen. The general synthetic strategy for the preparation of BIL 1-4 is simple and versatile and is shown in the Scheme above. A vital part of the synthesis of the base-tethered ionic liquids involves the use of 2-diisopropylaminoethyl chloride reacting with a chosen nucleophilic reagent and is facilitated by the neighbouring group participation from the diisopropylamino moiety. The synthetic strategy for the preparation of BIL 1, 2 and 4 takes into account the ability to selectively quaternise the pendant amino, imidazolyl or pyridyl groups as against the diisopropylalkylamino group which is non-nucleophiolic in nature. The synthetic strategy for the preparation of BIL 3 makes use of the insolubility of the mono-quaternised diamine which precipitates out of toluene (solvent) thereby preventing it from further reaction with the alkyl halide. In all cases the halide anion associated with the quaternary ammonium salts was subjected to metathesis with lithium bis-triflimide to generate base tethered ionic liquids BIL 1-4.

EXAMPLE 10

A group of ionic liquids similar to those given in Example 9 is as follows:

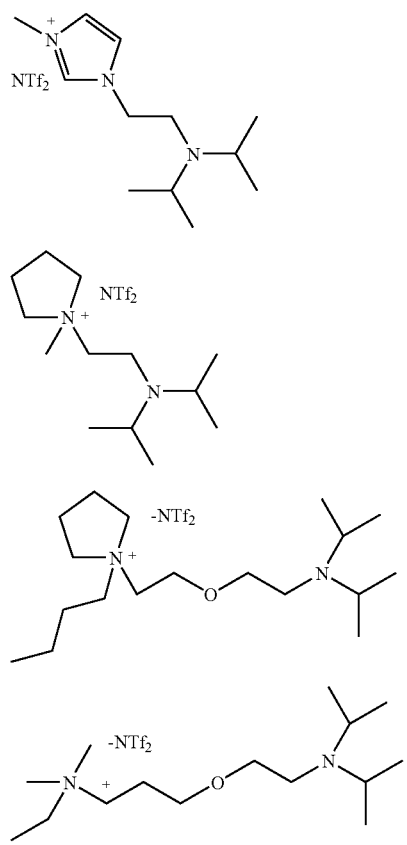

The physical properties of these ionic liquids are given in the table below. All of them are viscous room temperature ionic liquids and are pale yellow in colour.

Figure 3:
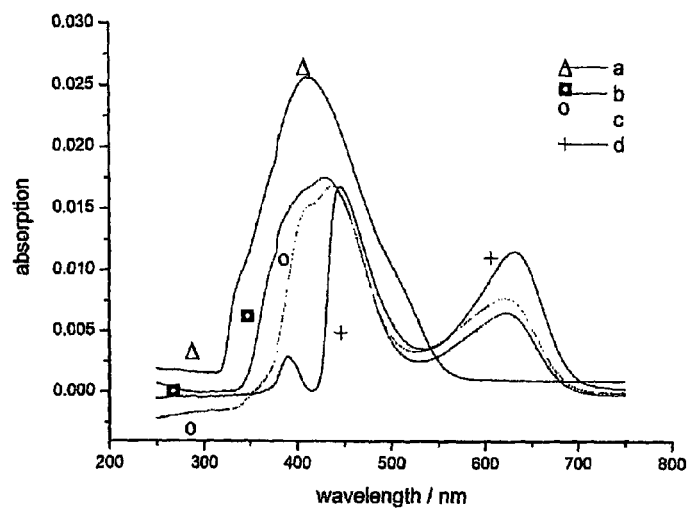

The relative base strength of these ionic liquids was measured by the aid of the universal indicator. A series of similar indicators had been used before to estimate the basicity of dicyanamide ionic liquids. FIG. 3 shows the manner in which the UV/Vis spectral characteristics of the universal indicator change with the nature of the basic ionic liquids.

These UV/Vis spectra give an indication of how the base strength of the pendant amino group varies with chain length and/or nature of the atoms in the chain. This can be explained by the fact that electronic repulsion between two cations (in the protonated state) decreases with increasing chain length, leading to higher basicity. The short wave-length band (~400-460 nm) represents the 'proton attached form' of the dye of the indicator while the long wave-length band (~620-640 nm) represents the 'deprotonated form' of the dye. The growth of the long wave-length band increases with the length of the chain between the two nitrogen atoms. Furthermore, long wave-length band is also associated with a small bathochromic shift. We have qualitatively shown here how the basicity of an ionic liquid can be tuned to a certain extent by simply changing the distance between the two nitrogen atoms without having to vary the nature of the dialkylamino group.

Figure 4:
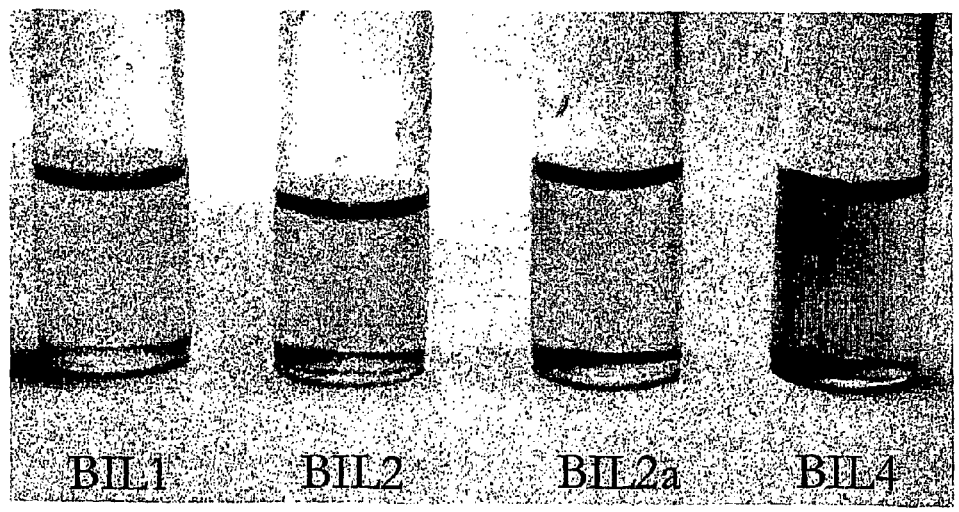

The visual colour changes that can be seen when Universal indicator interacts with basic ionic liquids, is depicted in FIG. 4.

Base Catalysed or Promoted Reactions

EXAMPLE 11

A use of the Mannich reaction in ionic liquids is in the synthesis of Tramadol (an analgesic).

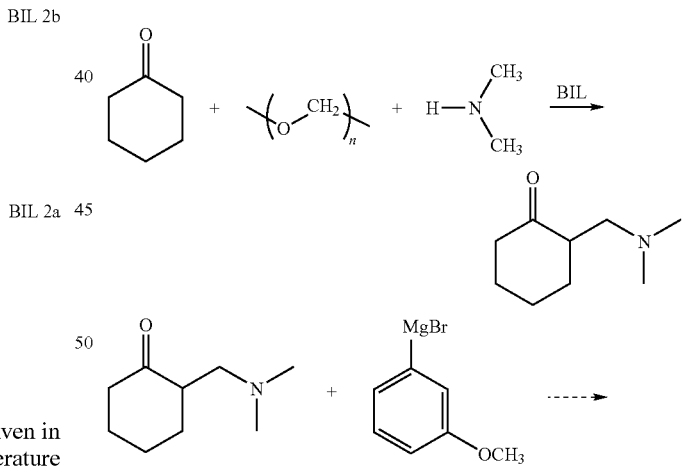

|  | Ionic liquid | | | | | | | |
| --- | --- | --- | --- | --- | --- | --- | --- | --- |
|  | BIL 1 | BIL 1a | BIL 1b | BIL 2 | BIL 2a | BIL 2b | BIL 3 | BIL 4 |
| Melting point | −73° C. | 33° C.* | −28° C. | −77° C. | −77° C. | −73° C. | −59° C. | −82° C. |
| Viscosity/cP | 540 | 417 | 313 | 398 | 330 | 310 | 475 | 195 |
| Density/g cm$^{-3}$ | 1.300 | 1.354 | 1.311 | 1.277 | 1.245 | 1.242 | 1.319 | 1.247 |

*ionic liquid BIL 1a is supercooled with a freezing point of −10° C.
Viscosity and density data at 25° C. on base-tethered ionic liquids BIL 1-4

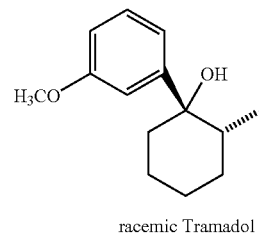

racemic Tramadol

EXAMPLE 12

Another classical reaction is the Robinson annulation. This involves a Michael reaction of an unsaturated ketone with a ketone followed by an internal aldol condensation. The reaction is typically carried out in solvents such as alcohols and in some cases, dipolar aprotic solvents such as DMF or DMSO are necessary. The Robinson annulation is a two step reaction and the intermediate Michael product is not normally isolated.

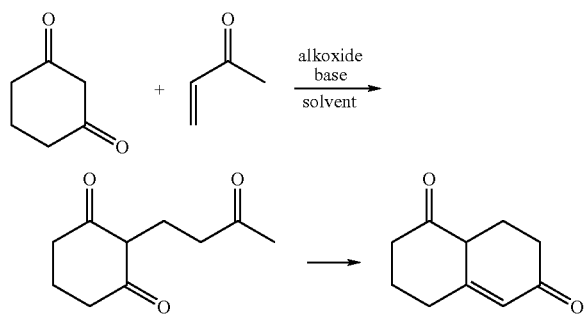

The Robinson annulation above was carried out using a base ionic liquid. At room temperature, the Michael product was obtained in high yield in under 5 minutes. This was considerably faster than a similar reaction carried in ethanol. The aldol condensation only occurred in the ionic liquid when the temperature was raised to 80° C. This reaction can also be carried out with a basic ionic liquid including but not limited to those in Examples 1-4.

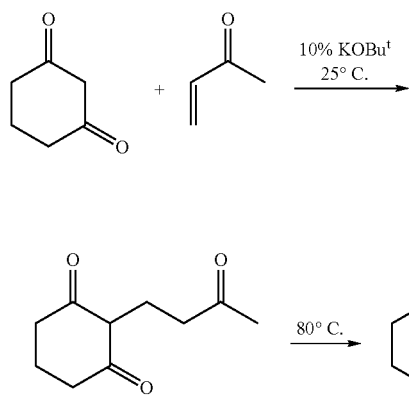

EXAMPLE 13

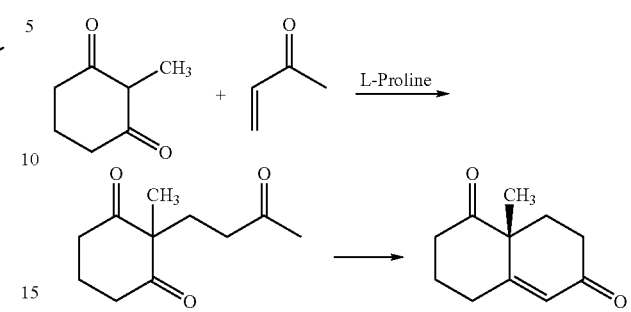

Proline is known to catalyse the reaction of 2-methylcyclohexy 1,3-dione with MVK and is reported to give a 49% yield of the annulated product (70% ee) in DMSO at 35° C. This reaction was attempted in a basic ionic liquid and the Michael reaction worked efficiently. This reaction can also be carried out with a basic ionic liquid including but not limited to those in Examples 1-4.

EXAMPLE 14

The condensation of acetone to isophorone can be performed in basic ionic liquids.

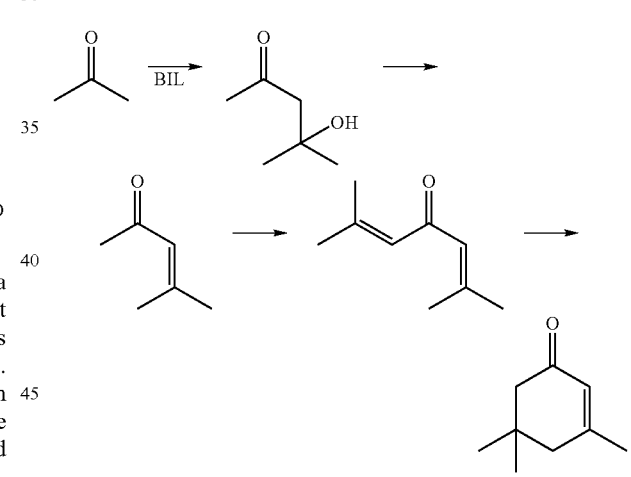

BIL = Basic ionic liquid

The condensation of cyclohexanone is a more complex.

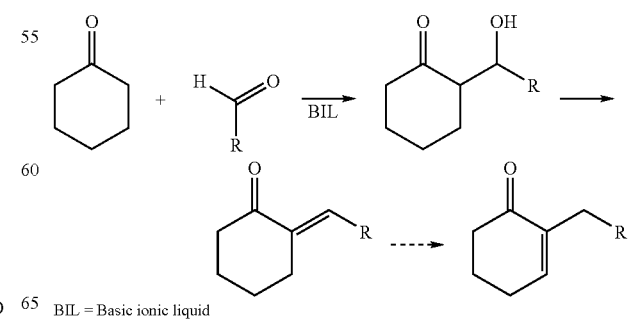

BIL = Basic ionic liquid

25
-continued
Side Reaction
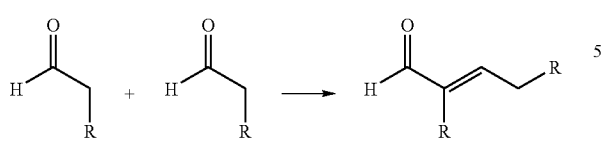
The Basic ionic liquids acts as both a catalyst and solvent
BIL = Basci ionic liquid
26
-continued
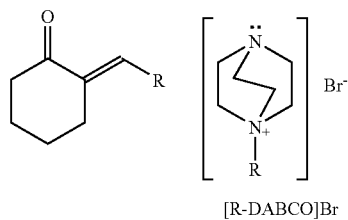
[R-DABCO]Br
EXAMPLE 15
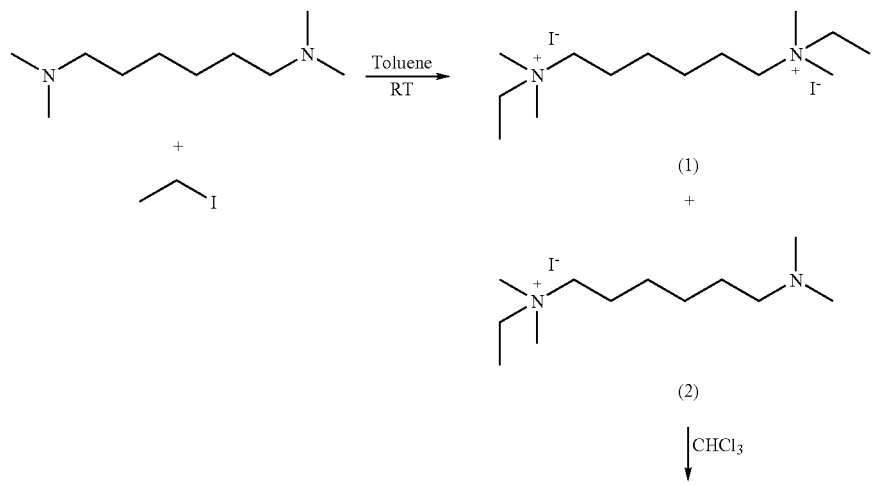
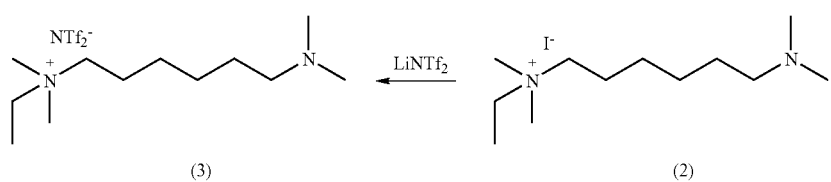

Synthesis of a basic ionic liquid based on tetramethylhexane-1,6-diamine synthesised according to the above procedure. These ionic liquids are stronger bases that the DABCO, or DMAP ionic liquids due to the greater separation between the cationic centre and the basic functional group.

EXAMPLE 16

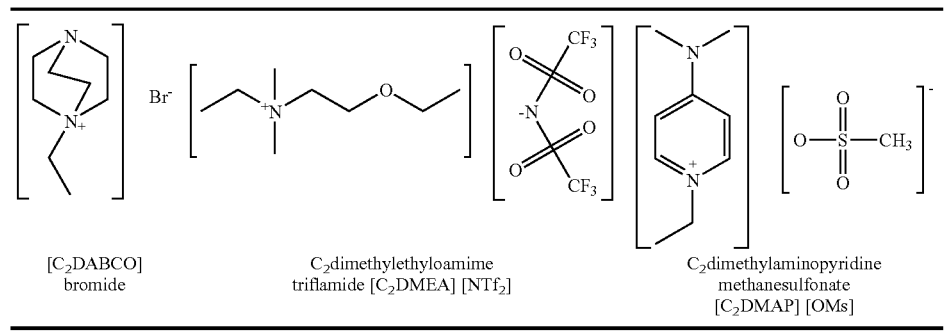

[C₂DABCO] bromide

C₂dimethylethyloamime triflamide [C₂DMEA] [NTf₂]

C₂dimethylaminopyridine methanesulfonate [C₂DMAP] [OMs]

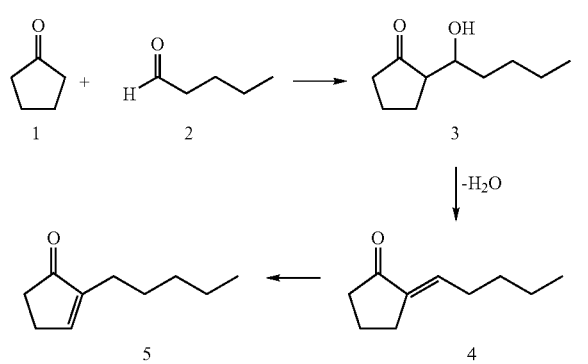

In a typical procedure, cyclopntanone (10 mmol), ionic liquids 1 g and catalyst (base or acid) were stirred together at desired temperature, after attainment of the temperature a known quantity of pentanal was added dropwise to avoid the self-condensation of the reactive aldehyde. Small aliquots of sample were withdrawn and extracted with water-hexane mixture. The organic layer was then passed through MgSO₄ plug and then was analysed by a gas chromatography. The compounds were identified using standards or by GC-MS. Heterogenous basic catalyst HT [hydrotalcite (Mg/Al atomic ratio=2)] and Zn(proline)₂ were prepared as reported procedures [Tichit et al., J. Catal., 219 (2003) 167] [Darbre et al., Chem. Commun., 2003, 1090], respectively.

The ionic liquids used in the above experiments were hydrophilic in nature and due to the presence of the nucleophilic nitrogen, they were also capable of catalysing the aldol condensation. The NMR spectroscopy revealed that the ionic liquids remain intact after the reaction so that these can be used further for the next cycle provided the products are separated by distillation. It is also possible to make these ionic liquids hydrophobic by replacing the anions, Br⁻ or [OMs]⁻ by the [NTf₂]⁻ anion. The basic ionic liquids give superior yield and selectivity in the crossed aldol reaction.

Thus, aldol chemistry route to the synthesis of dihydrojasmone in ionic liquids catalysed by proline offers excellent yields of MDJ-1. It is also possible to obtain MDJ-2 via catalytic distillation and can be viewed as one pot synthesis.

EXAMPLE 17

The Heck coupling to give lilial was very successful.

Heck reaction

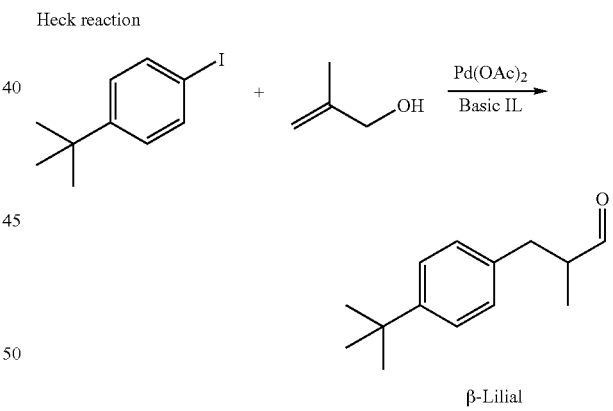

β-Lilial

| Expt | Ionic Liquids | Ketone/ald., mol | Catalyst | Reaction Temp C. | Time h | Wt % Conv. | Sel. |
|------|---------------|-----|----------|---------|--------|-------|------|
| SA4  | —             | 1   | 2M NaOH  | 80      | 3      | 85    | 85   |
| SA23 | —             | 4   | Ca(OH)₂  | 80      | 3      | 80    | 70   |
| SA1  | [C₄DABCO] Br  | 1   | —        | 80      | 3      | 99    | 90   |
| SA5  | [C₂DABCO] Br  | 1   | —        | 80      | 18     | 85    | 85   |
| SA6  | [C₂DMAP][OMs] | 1   | —        | 80      | 3      | 30    | 60   |

Knoevenagel reaction

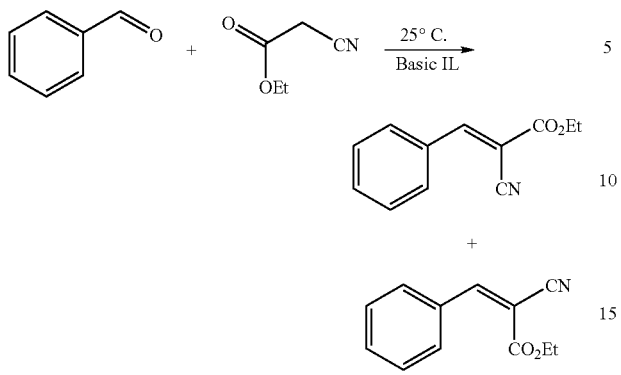

The reaction of b-methallyl alcohol with 4-t-butyliodobenzene was examined at 95° C. using palladium acetate as the catalyst. 4-t-Butyliodobenzene (5 mM) and b-methallyl alcohol (5.1 mM) and $Pd(OAc)_2$ (0.05 mM) were added to BIL 2 (10 mM) ionic liquid in a Schlenk tube. The sealed reaction vessel was heated at 95° C. for 10 h with stirring. The cooled reaction mixture was extracted with cyclohexane (4×5 ml) to remove products from the ionic liquid. Evaporation of the solvent from combined cyclohexane extracts yielded the products.

The conversion to lilial was ~32% when BIL 1 was used as the reaction medium. This is probably due to the reduced basicity of the pendant diisopropylamino group because of its proximity to the quaternary nitrogen atom. However the conversion to lilial increased dramatically to 84% when the Heck coupling was carried out under identical conditions in BIL 2. The extended length between quaternary nitrogen and the basic nitrogen and the contribution of the oxygen atom in the middle of the chain towards the overall basicity of the pendent amino group may account for this observation (see below).

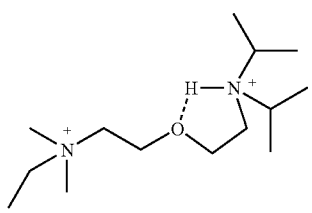

Stabilisation of the protonated base by the oxygen atom in the chain

Similarly the Knoevenagel reaction as shown above was carried out in BIL 1 obtaining near quantitative yields. Benzaldehyde (4 mM) and ethylcyano acetate (4.1 mM) were added to BIL 1(1 ml) in a Schlenk tube which was then stoppered and stirred at room temperature overnight. The products were extracted into cyclohexane (4×4 ml) and evaporation of the solvent from combined cyclohexane extracts yielded the products.

Selectivity for the reaction was also excellent exhibiting 99:1 ratios for the two possible products. The basicity of BIL 1 was sufficient to carry out the Knovenagel reaction even though the two nitrogens are separated only by a two carbon chain. It is also noteworthy that BIL 1 failed to deprotonate the dye present in the Universal indicator.

EXAMPLE 18

N-butyl-N-((N',N'-diisopropylaminoethoxy)-ethyl)-pyrrolidinium bistrifluoromethanesulfonylamide

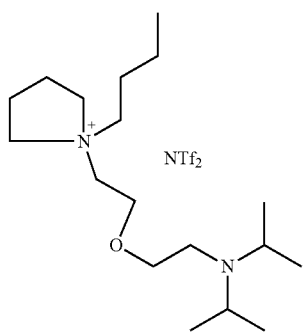

EXAMPLE 19

Improvement to Hydrogenation Reactions

Hydrogentation (Using BIL)

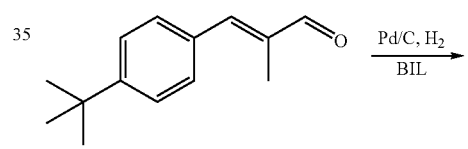

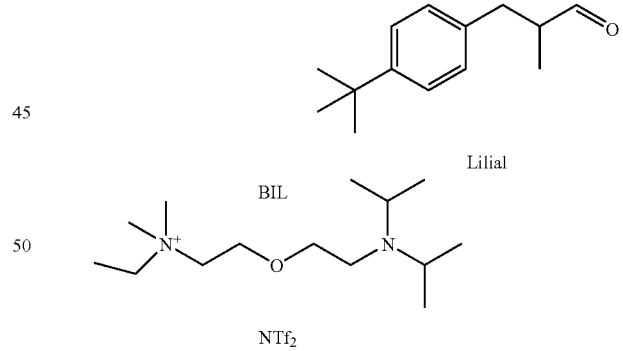

Using traditional base in [mbpyrr][$NTf_2$]

| Base | Yield % |
| --- | --- |
| No base | 62 |
| $Et_3N$ | 55 |
| Hunig's | 97 |
| 2,6-dimethylmorpholine | 85* |

*All Lilial was converted to Fenpropimorph

Using basic ionic liquids

| BIL | Iodide | IL | Yield % |
|---|---|---|---|
| 100% | — | — | 52 |
| 50% | — | 50% | 93 |
| — | 50% | 50% | 28 |
| 1% | — | 99% | 89 |

Employment of a basic ionic liquid gave improved yields.

The invention claimed is:

1. A method of performing a base-catalyzed chemical reaction, comprising performing the base-catalyzed chemical reaction in the presence of an ionic liquid that is both a solvent and a catalyst for the base-catalyzed chemical reaction, wherein the ionic liquid comprises at least one species of cation and at least one species of anion, the cation of the ionic liquid comprising (i) a positively charged moiety and (ii) a basic moiety.

2. The method according to claim 1, wherein the ionic liquid comprises a mixture of one or more cations having a basic moiety and a positively charged moiety.

3. The method according to claim 1, wherein the ionic liquid comprises a mixture of one or more anions.

4. The method according to claim 1, wherein the ionic liquid further comprises a mixture of one or more ionic liquids composed of a cation and an anion.

5. The method according to claim 1, wherein the chemical reaction is selected from the group consisting of the Heck Reaction, Suzuki Coupling, nucleophilic displacement reactions, hydrolysis, esterification, transesterification aldol reactions, epoxidation, hydrogenation, condensation, oxidation reduction, hydration, dehydration, substitution, aromatic substitution, addition (including to carbonyl groups), elimination, polymerization, depolymerization, oligomerization, dimerization, coupling, electrocyclic, isomerization, carbene formation, epimerization, inversion, rearrangement, photochemical, microwave assisted, thermal, sonochemical, and disproportionation reactions.

6. The method according to claim 1 wherein the ionic liquid is represented by the formula:

[Cat$^+$-Z-Bas][X$^-$]

wherein:
Cat$^+$=positively charged moiety;
Bas=basic moiety;
Z=a covalent bond joining Cat$^+$ and Bas or 1, 2, or 3 aliphatic divalent linking groups each containing 1 to 10 carbon atoms and each optionally one, two or three oxygen atoms;
X$^-$=anion; and
with the proviso that Bas is not —OH.

7. The method according to claim 6, wherein Bas comprises at least one nitrogen, phosphorus, sulfur, oxygen or boron atom.

8. The method according to claim 7, wherein Bas comprises at least one primary, secondary, or tertiary amino group.

9. The method according to claim 7, wherein Bas is selected from the group consisting of —N(R$_1$)(R$_2$), and —P(R$_1$)(R$_2$)(R$_3$); and R$_1$, R$_2$, and R$_3$ can be the same or different and are each independently selected from the group consisting of hydrogen, linear or branched alkyl, linear or branched cycloalkyl, linear or branched aryl, and linear or branched substituted aryl.

10. The method according to claim 9, wherein R$_1$, R$_2$ and R$_3$ are each selected from the group consisting of hydrogen, methyl, ethyl, isopropyl, propyl, butyl, sec-butyl, isobutyl, pentyl, hexyl, cyclohexyl, benzyl, and phenyl.

11. The method according to claim 9, wherein Bas is selected from the group consisting of —N(CH$_3$)$_2$ and —N(CH(CH$_3$)$_2$)$_2$.

12. The method according to claim 6, wherein Z is selected from the group consisting of linear or branched C$_1$ to C$_{18}$ alkanediyl, substituted alkanediyl, dialkanylether, and dialkanylketone.

13. The method according to claim 12, wherein Z is selected from the group consisting of —(CH$_2$—CH$_2$)—, —(CH$_2$—CH$_2$—CH$_2$)—, —(CH$_2$—CH$_2$—CH$_2$—CH$_2$)—, —(CH$_2$—CH$_2$—CH$_2$—CH$_2$—CH$_2$)—, —(CH$_2$—CH$_2$—CH$_2$—CH$_2$—CH$_2$—CH$_2$)—, —(CH$_2$—CH$_2$—O—CH$_2$—CH$_2$)—, and —(CH$_2$—CH$_2$—O—CH$_2$—CH$_2$—CH$_2$)—.

14. The method according to claim 6, wherein the Cat$^+$ moiety comprises a heterocyclic ring structure selected from the group consisting of imidazolium, pyridinium, pyrazolium, thiazolium, isothiazolinium, azathiozolium, oxothiazolium, oxazinium, oxazolium, oxaborolium, dithiazolium, triazolium, selenozolium, oxaphospholium, pyrollium, borolium, furanium, thiophenium, phospholium, pentazolium, indolium, indolinium, oxazolium, isooxazolium, isotriazolium, tetrazolium, benzofuranium, dibenzofuranium, benzothiophenium, dibenzothiophenium, thiadiazolium, pyrimidinium, pyrazinium, pyridazinium, piperazinium, piperidinium, morpholinium, pyranium, annolinium, phthalazinium, quinazolinium, quinazalinium, quinolinium, isoquinolinium, thazinium, oxazinium, and azaannulenium.

15. The method according to claim 14, wherein Cat$^+$-Z-Bas is selected from the group consisting of:

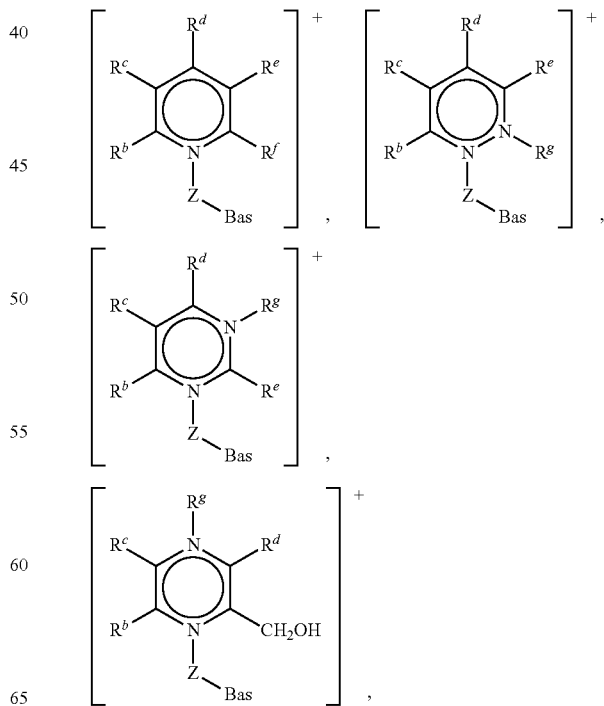

-continued

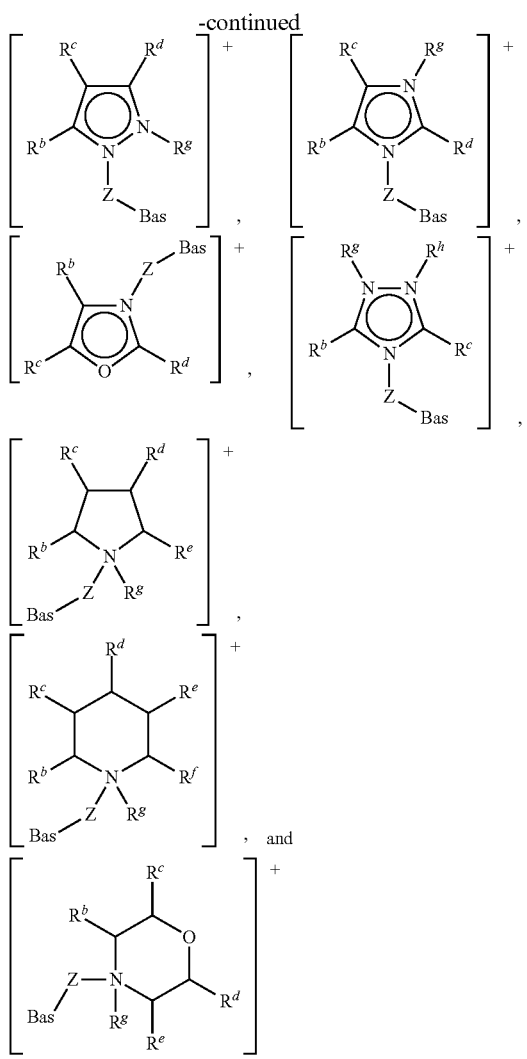

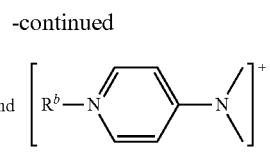

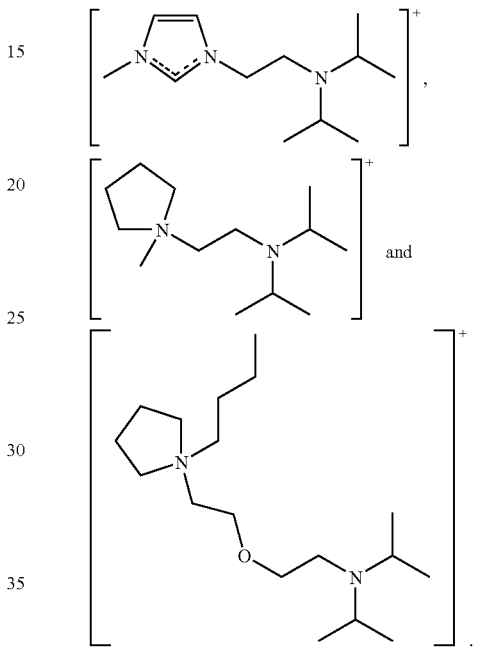

wherein:

$R^b$, $R^c$, $R^d$, $R^e$, $R^f$, $R^g$, and $R^h$ can be the same or different, and are each independently selected from the group consisting of hydrogen, a $C_1$ to $C_{40}$, straight chain or branched alkyl group, a $C_3$ to $C_8$ cycloalkyl group, and a $C_6$ to $C_{10}$ aryl group, wherein said alkyl, cycloalkyl or aryl groups are optionally substituted by one to three groups selected from the group consisting of: $C_1$ to $C_8$ alkoxy, $C_6$ to $C_{10}$ aryl, CN, OH, $NO_2$, $C_7$ to $C_{30}$ aralkyl and $C_7$ to $C_{30}$ alkaryl, or any two of $R^b$, $R^c$, $R_d$, $R_e$ and $R^f$ attached to adjacent carbon atoms form a methylene chain —$(CH_2)_q$— wherein q is an integer from 8 to 20.

16. The method according to claim 15, wherein the Cat$^+$-Z-Bas is selected from the group consisting of:

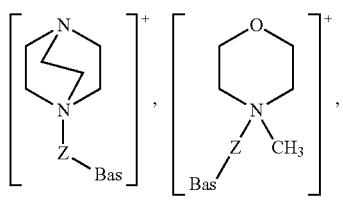

17. The method according to claim 15, wherein Cat$^+$-Z-Bas is selected from the group consisting of:

18. The method according to claim 14, wherein Cat$^+$ is obtained from at least one of alkylation, protonation and acylation of a precursor selected from the group consisting of imidazoles, pyridines, pyrazoles, thiazoles, isothiazoles, azathiozoles, oxothiazoles, oxazines, oxazolines, oxazoboroles, dithiozoles, triazoles, selenozoles, oxaphospholes, pyrroles, boroles, furans, thiophenes, phospholes, pentazoles, indoles, indolines, oxazoles, isooxazoles, isotriazoles, tetrazoles, benzofurans, dibenzofurans, benzothiophenes, dibenzothiophenes, thiadiazoles, pyrimidines, pyrazines, pyridazines, piperazines, piperidines, morpholenes, pyrans, annolines, phthalzines, quinazolines, quinoxalines, quinolines, isoquinolines, thazines, oxazines, and azaannulenes.

19. The method according to claim 6, wherein Cat$^+$ is an acyclic organic moiety.

20. The method according to claim 19 wherein the Cat$^+$ moiety comprises a group selected from the group consisting of amino, amidino, imino, guanidino, phosphino, arsino, stibino, alkoxyalkyl, alkylthio, alkylseleno, and phosphinimino.

21. The method according to claim 20, wherein Cat$^+$-Z-Bas is selected from the group consisting of:

$[N(Z\text{-}Bas)(R^b)(R^c)(R^d)]^+$ and $[P(Z\text{-}Bas)(R^b)(R^c)(R^d)]$ wherein: $R^b$, $R^c$, and $R^d$ are each independently selected from the group consisting of hydrogen, a $C_1$ to $C_{40}$, straight chain or branched alkyl group, a $C_3$ to $C_8$ cycloalkyl group, and a $C_6$ to $C_{10}$ aryl group, wherein said alkyl, cycloalkyl or aryl group is optionally substituted by one to three groups selected from the group consisting of $C_1$ to $C_6$ alkoxy, $C_6$ to $C_{10}$ aryl, CN, OH, $NO_2$, $C_7$ to $C_{30}$ aralkyl and $C_7$ to $C_{30}$ alkaryl; with the proviso that Bas is not —OH or —N(Et)$_2$.

22. The method according to claim 21, wherein Cat$^+$-Z-Bas is selected from the group consisting of:

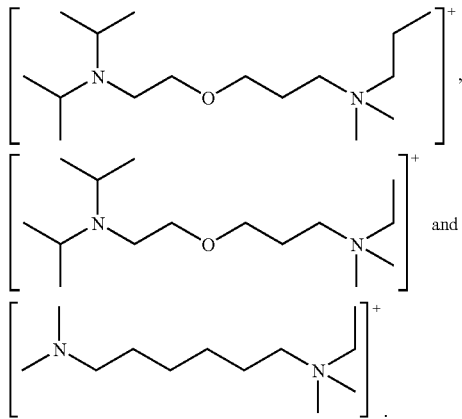

23. The method according to claim 20 wherein Cat$^+$-Z-Bas comprises a compound having a formula:

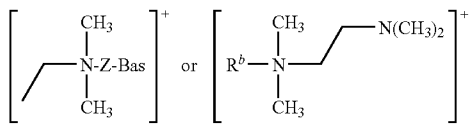

wherein: $R^b$ is selected from the group consisting of hydrogen, a $C_1$ to $C_{40}$, straight chain or branched alkyl group, a $C_3$ to $C_8$ cycloalkyl group, and a $C_6$ to $C_{10}$ aryl group, wherein said alkyl, cycloalkyl or aryl group is optionally substituted by one to three groups selected from the group consisting of $C_1$ to $C_6$ alkoxy, $C_6$ to $C_{10}$ aryl, CN, OH, $NO_2$, $C_7$ to $C_{30}$ aralkyl and $C_7$ to $C_{30}$ alkaryl.

24. The method according to claim 6, wherein Cat$^+$-Z-Bas is a compound of formula:

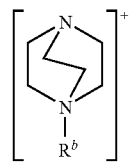

wherein: $R^b$ is selected from the group consisting of hydrogen, a $C_1$ to $C_{40}$, straight chain or branched alkyl group, a $C_3$ to $C_8$ cycloalkyl group, and a $C_6$ to $C_{10}$ aryl group, wherein said alkyl, cycloalkyl or aryl group is optionally substituted by one to three groups selected from the group consisting of $C_1$ to $C_6$ alkoxy, $C_6$ to $C_{10}$ aryl, CN, OH, $NO_2$, $C_7$ to $C_{30}$ aralkyl and $C_7$ to $C_{30}$ alkaryl.

25. The method according to claim 6, wherein $X^-$ is an alkylated or halogenated salt of a Group IB, IIIA, IVA, VA, VIA, or VIIA element.

26. The method according to claim 25 wherein $X^-$ the anion is selected from the group consisting of hydroxide, alkoxide, phenoxide, dicyanamide, borate, phosphate, nitrate, sulfate, triflate, halogenated copperate, antimonate, phosphite, substituted and unsubstituted metalloborane, substituted and unsubstituted carboxylate and triflate; and mixtures thereof.

27. The method according to claim 25, wherein $X^-$ is selected from the group consisting of $BF_4$, $PF_6$, $CF_3SO_3$, $CF_3COO$, $SbF_6$, $CuCl_2$, $A_5F_6$, $SO_4$, $CF_3CH_2CH_2COO$, $(CF_3SO_2)_3C$, $CF_3(CF_2)_3SO_3$, $[CF_3SO2]_2N$ and a metal inorganic anion.

28. The method according to claim 6, wherein, $X^-$ is selected from the group consisting of halide, triflate, bistrifluoromethanesulfonylamide [(CF$_3$SO$_2$)$_2$N] and alkylsulfonate [RSO$_3$].

29. The method according to claim 6, wherein $X^-$ is represented by the formula:

[X—R-Bas]- wherein R is a covalent bond joining X and Bas, or a linking group comprising 1 to 10 carbon atoms and optionally one, two or three oxygen atoms.

* * * * *

UNITED STATES PATENT AND TRADEMARK OFFICE
CERTIFICATE OF CORRECTION

PATENT NO.        : 8,609,572 B2                                      Page 1 of 1
APPLICATION NO.   : 11/794772
DATED             : December 17, 2013
INVENTOR(S)       : Earl et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 919 days.

Signed and Sealed this
Twenty-second Day of September, 2015

Michelle K. Lee
*Director of the United States Patent and Trademark Office*